(12) United States Patent
Novelli et al.

(10) Patent No.: US 8,071,721 B2
(45) Date of Patent: Dec. 6, 2011

(54) ANTIGENS AND ANTIBODIES ASSOCIATED TO PANCREATIC DUCTAL ADENOCARCINOMA

(75) Inventors: Francesco Novelli, Torino (IT); Barbara Tomaino, Rivarolo Canavese (IT); Paola Cappello, Torino (IT)

(73) Assignees: Ribovax Biotechnologies S.A., Petit-Lancy (CH); Bioline Diagnostici SRL, Torino (IT)

( * ) Notice: Subject to any disclaimer, the term of this patent is extended or adjusted under 35 U.S.C. 154(b) by 0 days.

(21) Appl. No.: 12/443,576

(22) PCT Filed: Sep. 28, 2007

(86) PCT No.: PCT/EP2007/060305
§ 371 (c)(1),
(2), (4) Date: Sep. 30, 2009

(87) PCT Pub. No.: WO2008/037792
PCT Pub. Date: Apr. 3, 2008

(65) Prior Publication Data
US 2010/0028907 A1  Feb. 4, 2010

(30) Foreign Application Priority Data

Sep. 29, 2006 (EP) .................................... 06121552
Dec. 20, 2006 (EP) .................................... 06126726

(51) Int. Cl.
*C07K 14/00* (2006.01)
*A61K 38/16* (2006.01)

(52) U.S. Cl. ........................................ 530/352; 530/350

(58) Field of Classification Search ........................ None
See application file for complete search history.

(56) References Cited

U.S. PATENT DOCUMENTS 5,753,446 A * 5/1998 Johnson ........................ 435/7.1

OTHER PUBLICATIONS

Eigenbrodt et al (The EMBO J 2:1565-1570, 1983.*
Electrophoresis, 21:2622-36, 2000.*
Rush et al, Nature BioTech. 23: 94-101, online published Dec. 2004.*
Marcus et al , Electrophoresis 21:2622-2636, 2000.*
Stasyk et al, Mole Bio Cell, 16: 4765-4780, 2005.*
Giallongo et al., "Molecular cloning and nucleotide sequence of a full-length cDNA for human α enolase", *Proc. Natl. Acad. Sci. USA*, 83, 6741-5 (1986).
International Search Report in PCT/EP2007/060305 dated Feb. 12, 2008.
Marcus et al., "Identification of platelet proteins separated by two-dimensional gel electrophoresis and analyzed by matrix assisted laser desorption/ionization-time of flight-mass spectrometry and detection of tyrosine-phosphorylated proteins", *Electrophoresis*, 21, 2622-2636 (2000).
Shen et al., "Protein expression profiles in pancreatic adenocarcinoma compared with normal pancreatic tissue and tissue affected by pancreatitis as detected by two-dimensional gel electrophoresis and mass spectrometry", *Cancer Research*, 64(24):9018-9026 (2004).
Subramanian et al., "Structural analysis of α-enolase", *J. Biol. Chem.*, 275(8):5958-5965 (2000).
Tanaka et al., "Chicken α-enolase but not β-enolase has a src-dependent tyrosine-phosphorylation site: cDNA cloning and nucleotide sequence analysis", *J. Biochem.*, 117, 554-559 (1995).
Tomaino et al., "Autoantibody signature in human ductal pancreatic adenocarcinoma", *Journal of Proteome Research*, 6, 4025-4031 (2007).
Walter et al., "Autoreactive epitopes within the human α-enolase and their recognition by sera from patients with endometriosis", *Journal of Autoimmunity*, 8, 931-945 (1995).

* cited by examiner

*Primary Examiner* — Misook Yu
*Assistant Examiner* — Lei Yao
(74) *Attorney, Agent, or Firm* — Marshall, Gerstein & Borun LLP

(57) ABSTRACT

The present invention provides novel human protein antigens and related antibodies that have been identified as being specifically expressed in association to human Pancreatic Ductal Adenocarcinoma (PDA). In particular, novel phosphorylated isoforms of alpha-enolase have been identified in transformed cell lines of pancreatic origin and antibodies binding such isoforms are specifically present in the sera of PDA patients. These proteins and antibodies can be useful for the diagnosis and the treatment of PDA and other cancers having common molecular features.

3 Claims, 6 Drawing Sheets

Figure 2
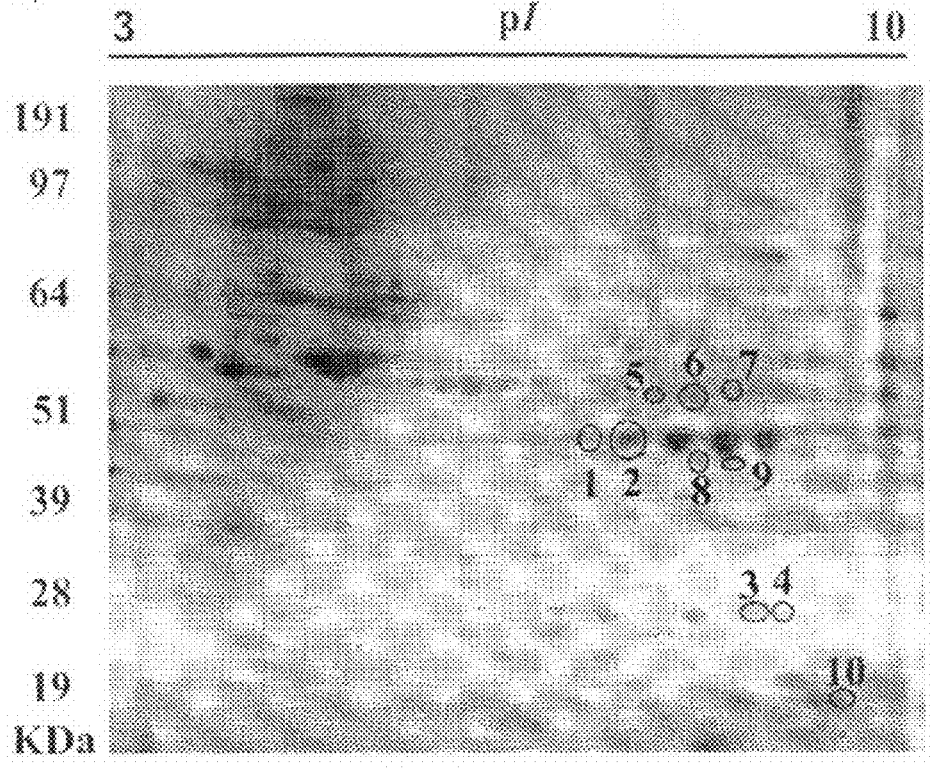
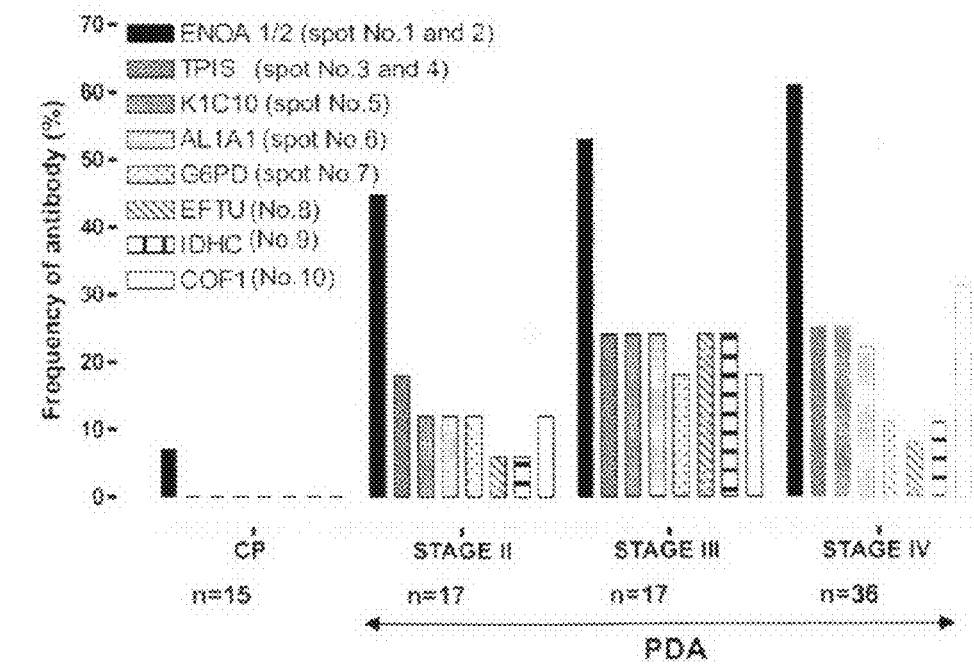

Figure 3

```
              10         20         30         40         50         60
ENOA  MSILKIHAREIFDSRGNPTVEVDLFTSKGLFRAAVPSGASTGIYEALELRDNDKTRYMGK
      ::  ::  ::::::::::::::::: .:::::::::::::::::::::::::.::  ::..:::
ENOG  MSIEKIWAREILDSRGNPTVEVDLYTAKGLFRAAVPSGASTGIYEALELRDGDKQRYLGK 70         80         90        100        110        120
ENOA  GVSKAVEHINKTIAPALVSKKLNVTEQEKIDKLMIEMDGTENKSKFGANAILGVSLAVCK
      ::  :::.:::.:::::::.:.  :.:.::::.:.::.::::::::::::::::::::::
ENOG  GVLKAVDHINSTIAPALISSGLSVVEQEKLDNLMLELDGTENKSKFGANAILGVSLAVCK 130        140        150        160        170        180
ENOA  AGAVEKGVPLYRHIADLAGNSEVILPVPAFNVINGGSHAGNKLAMQEFMILPVGAANFRE
      :::.:..::::::::..::::::.  :::::::::::::::::::::::::::::: .::.
ENOG  AGAAERELPLYRHIAQLAGNSDLILPVPAFNVINGGSHAGNKLAMQEFMILPVGAESFRD 190        200        210        220        230        240
ENOA  AMRIGAEVYHNLKNVIKEKYGKDATNVGDEGGFAPNILENKEGLELLKTAIGKAGYTDKV
      :::.:::::::.::.::::::::::::::::::::::::::.. .:: :: ::::::..:.
ENOG  AMRLGAEVYHTLKGVIKDKYGKDATNVGDEGGFAPNILENSEALELVKEAIDKAGYTEKI 250        260        270        280        290        300
ENOA  VIGMDVAASEFFRSGKYDLDFKSPDDPSRYISPDQLADLYKSFIKDYPVVSIEDPFDQDD
      ::::::::::::.. ::::::::::::  :::::  ::. :: .:.::::::::::::::
ENOG  VIGMDVAASEFYRDGKYDLDFKSPTDPSRYITGDQLGALYQDFVRDYPVVSIEDPFDQDD 310        320        330        340        350        360
ENOA  WGAWQKFTASAGIQVVGDDLTVTNPKRIAKAVNEKSCNCLLLKVNQIGSVTESLQACKLA
      ..::.:::.. :::::::::::::::::::  :::.::::::::::::::::::  ::::::
ENOG  WAAWSKFTANVGIQIVGDDLTVTNPKRIERAVEEKACNCLLLKVNQIGSVTEAIQACKLA 370        380        390        400        410        420
ENOA  QANGWGVMVSHRSGETEDTFIADLVVGLCTGQIKTGAPCRSERLAKYNQLLRIEEELGSK
      :  ::::::::::::::::::::::::::::::::::::::::::::::::..::::::::..
ENOG  QENGWGVMVSHRSGETEDTFIADLVVGLCTGQIKTGAPCRSERLAKYNQLMRIEEELGDE

430
ENOA  AKFAGRNFRNPLAK
      :..::.:::::
ENOG  ARFAGHNFRNPSVL
```

Figure 4

```
              10         20         30         40         50         60
ENOA  MSILKIHAREIFDSRGNPTVEVDLFTSKGLFRAAVPSGASTGIYEALELRDNDKTRYMGK
                    n         gp        g   gk  n          p n
                    g         k          p  pp  g           ⓘ g
                    g         p                 d             d
                    k                            ⓡ            k
                    p                            p            p
                                                              ⓜ
                                                              ⓘ

70         80         90        100        110        120
ENOA  GVSKAVEHINKTIAPALVSKKLNVTEQEKIDKLMIEMDGTENKSKFGANAILGVSLAVCK
      ⓜ           k          k          g          g          g
      k           p          p          k          k  p       k
      p                      p          p                     p 130        140        150        160        170        180
ENOA  AGAVEKGVPLYRHIADLAGNSEVILPVPAFNVINGGSHAGNKLAMQEFMILPVGAANFRE
              p          p           p            g
                                                  k
                                                  p 190        200        210        220        230        240
ENOA  AMRIGAEVYHNLKNVIKEKYGKDATNVGDEGGFAPNILENKEGLELLKTAIGKAGYTDKV
           n            n            p                  g         nn
           g            g                                p        gg
           p            k                                         pk
                        ⓘ                                         ⓘⓘ
                        p                                         p 250        260        270        280        290        300
ENOA  VIGMDVAASEFFRSGKYDLDFKSPDDPSRYISPDQLADLYKSFIKDYPVVSIEDPFDQDD
              g       n ⓘ    n      n n n        g g        g    n
              p       p p    g      p g g        p p        ⓡ    g
                                      d d                   p    p
                                      k k
                                      p p 310        320        330        340        350        360
ENOA  WGAWQKFTASAGIQVVGDDLTVTNPKRIAKAVNEKSCNCLLLKVNQIGSVTESLQACKLA
           g k              g g            g            n  g g
           p p              k k            p            g  p k
                            p p                         k     p
                                                        p 370        380        390        400        410        420
ENOA  QANGWGVMVSHRSGETEDTFIADLVVGLCTGQIKTGAPCRSERLAKYNQLLRIEEELGSK
              g   n g g         p      g            p           g
              p   g p p                                         p
                  p                                             ⓘ

430
ENOA  AKFAGRNFRNPLAK
``` n  NetPhos                    ⓜ Identified in Molina H et al., 2007
g  GPS                         ⓡ Identified in Rush J et al., 2005
d  dbPTM                       ⓘ Identified in the ENOA Isoform
k  NetPhosk                       3 isolated from CF-PAC-1 cell
p  PSPP                           extracts by 2-DE Figure 5
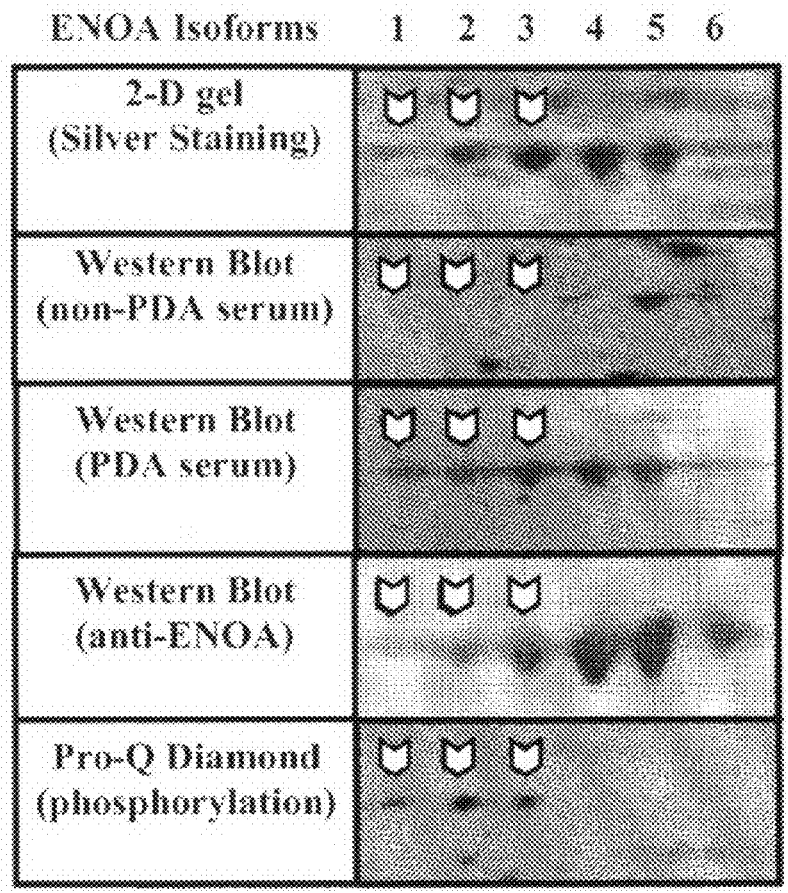
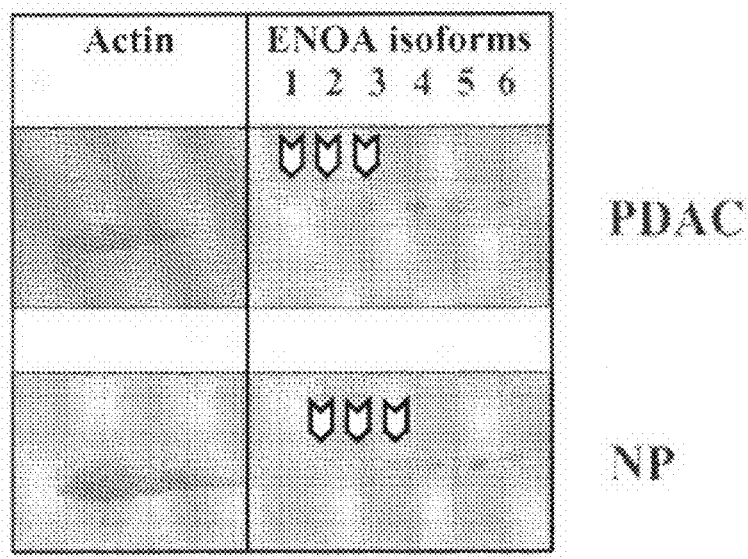

SEQUENCE LISTING

<160> NUMBER OF SEQ ID NOS: 2

<210> SEQ ID NO 1
<211> LENGTH: 434
<212> TYPE: PRT
<213> ORGANISM: Homo sapiens

<400> SEQUENCE: 1

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
         35                  40                  45

Leu Arg Asp Asn Asp Lys Thr Arg Tyr Met Gly Lys Gly Val Ser Lys
 50                  55                  60

Ala Val Glu His Ile Asn Lys Thr Ile Ala Pro Ala Leu Val Ser Lys
 65                  70                  75                  80

Lys Leu Asn Val Thr Glu Gln Glu Lys Ile Asp Lys Leu Met Ile Glu
                 85                  90                  95

Met Asp Gly Thr Glu Asn Lys Ser Lys Phe Gly Ala Asn Ala Ile Leu
             100                 105                 110

Gly Val Ser Leu Ala Val Cys Lys Ala Gly Ala Val Glu Lys Gly Val
         115                 120                 125

Pro Leu Tyr Arg His Ile Ala Asp Leu Ala Gly Asn Ser Glu Val Ile
     130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                 165                 170                 175

Asn Phe Arg Glu Ala Met Arg Ile Gly Ala Glu Val Tyr His Asn Leu
             180                 185                 190

Lys Asn Val Ile Lys Glu Lys Tyr Gly Lys Asp Ala Thr Asn Val Gly
         195                 200                 205

Asp Glu Gly Gly Phe Ala Pro Asn Ile Leu Glu Asn Lys Glu Gly Leu
     210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                 245                 250                 255

Tyr Asp Leu Asp Phe Lys Ser Pro Asp Asp Pro Ser Arg Tyr Ile Ser
             260                 265                 270

Pro Asp Gln Leu Ala Asp Leu Tyr Lys Ser Phe Ile Lys Asp Tyr Pro
         275                 280                 285

Val Val Ser Ile Glu Asp Pro Phe Asp Gln Asp Asp Trp Gly Ala Trp
     290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                 325                 330                 335

Cys Asn Cys Leu Leu Leu Lys Val Asn Gln Ile Gly Ser Val Thr Glu
             340                 345                 350

Ser Leu Gln Ala Cys Lys Leu Ala Gln Ala Asn Gly Trp Gly Val Met
         355                 360                 365

Val Ser His Arg Ser Gly Glu Thr Glu Asp Thr Phe Ile Ala Asp Leu
     370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                 405                 410                 415

Leu Gly Ser Lys Ala Lys Phe Ala Gly Arg Asn Phe Arg Asn Pro Leu
             420                 425                 430

Ala Lys

<210> SEQ ID NO 2
<211> LENGTH: 434

```
<212> TYPE: PRT
<213> ORGANISM: Homo sapiens

<400> SEQUENCE: 2

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Gly Asp Lys Gln Arg Tyr Leu Gly Lys Gly Val Leu Lys
        50                  55                  60

Ala Val Asp His Ile Asn Ser Thr Ile Ala Pro Ala Leu Ile Ser Ser
65                  70                  75                  80

Gly Leu Ser Val Val Glu Gln Glu Lys Leu Asp Asn Leu Met Leu Glu
                85                  90                  95

Leu Asp Gly Thr Glu Asn Lys Ser Lys Phe Gly Ala Asn Ala Ile Leu
                100                 105                 110

Gly Val Ser Leu Ala Val Cys Lys Ala Gly Ala Ala Glu Arg Glu Leu
            115                 120                 125

Pro Leu Tyr Arg His Ile Ala Gln Leu Ala Gly Asn Ser Asp Leu Ile
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
                180                 185                 190

Lys Gly Val Ile Lys Asp Lys Tyr Gly Lys Asp Ala Thr Asn Val Gly
            195                 200                 205

Asp Glu Gly Gly Phe Ala Pro Asn Ile Leu Glu Asn Ser Glu Ala Leu
        210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Thr Asp Pro Ser Arg Tyr Ile Thr
                260                 265                 270

Gly Asp Gln Leu Gly Ala Leu Tyr Gln Asp Phe Val Arg Asp Tyr Pro
            275                 280                 285

Val Val Ser Ile Glu Asp Pro Phe Asp Gln Asp Asp Trp Ala Ala Trp
        290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
                340                 345                 350

Ala Ile Gln Ala Cys Lys Leu Ala Gln Glu Asn Gly Trp Gly Val Met
            355                 360                 365

Val Ser His Arg Ser Gly Glu Thr Glu Asp Thr Phe Ile Ala Asp Leu
        370                 375                 380

Val Val Gly Leu Cys Thr Gly Gln Ile Lys Thr Gly Ala Pro Cys Arg
385                 390                 395                 400
```

```
Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
                420                 425                 430

Val Leu
```

ANTIGENS AND ANTIBODIES ASSOCIATED TO PANCREATIC DUCTAL ADENOCARCINOMA

CROSS-REFERENCE TO RELATED APPLICATIONS

This is the U.S. national phase of International Application No. PCT/EP2007/060305, filed Sep. 28, 2007, which claims the benefit of European Patent Application No. 06126726.6, filed Dec. 20, 2006 and European Patent Application No. 06121552.1, filed Sep. 29, 2006.

TECHNICAL FIELD

The present invention relates to novel means for diagnosing and treating human cancers, in particular those of pancreatic origin.

BACKGROUND OF THE INVENTION

Pancreatic Ductal Adenocarcinoma (PDA) is the most frequent pancreatic cancer and the fourth cause of cancer death in the United States and Europe. Most patients die within 12 months, and only 2% survive five years after diagnosis. Pancreatectomy remains the cornerstone of PDA management and chemotherapy but provides marginal survival benefit (Laheru D and Jaffee M, 2005; Kleef J et al., 2006).

Despite improved surgical and medical management (including the use of monoclonal antibodies, vaccines, and chemotherapy), there are still few and poorly reliable markers for early PDA diagnosis. The most widely used serological marker for pancreatic cancer diagnosis is sialylated Lewis blood group antigen CA 19-9, but its use is mostly directed toward monitoring response to therapy, rather than PDA diagnosis. In fact, this antigen may also be present at elevated concentrations in the sera from patients affected by benign pancreatic diseases (such as chronic pancreatitis or biliary obstruction) providing false positives, and it cannot be used in all cases because it is not expressed at all in 5-10% of the population (Okusaka T et al., 2006).

It is for these reasons that alternative biomarkers are under evaluation for use in PDA diagnosis, with the aim to limit invasive procedures such as biopsies and histopathological evaluation (Bouvet M, 2004; Brand R, 2001; Goggins M, 2005; Leung T et al., 2005), and for evaluating drug candidates (Cohen S and Meropol N, 2002; Jimeno A and Hidalgo M, 2006).

Various technologies have been recently employed for the identification of candidate PDA biomarkers using large scale analysis of protein expression (either based on RNA or protein levels). In particular, proteomic technologies have been used to detect antigens that elicit a humoral response in the sera of PDA patients by comparing the proteins that are resolved by two-dimensional gel electrophoresis (2-DE), recognized by serum antibodies from cancer patients, and identified using Mass Spectrometry (Gorg A et al., 2004; Graham D et al., 2005). Variants of this approach for protein separation, selection and characterization have been described under different names in the literature, such as SERPA (Klade C et al., 2001), PROTEOMEX (Lichtenfels R et al., 2003), or SPEAR (Unwin R et al., 2003).

The work hypothesis common to these methodologies is that, by characterizing the B cell repertoire against antigens specifically expressed by cancers (the so-called human cancer immunome), it should be possible to define specific targets that are involved in cancer immunosurveillance and immunoediting, and to understand the mechanisms leading to uncontrolled cell proliferation and metastasis (Drake C et al., 2006; Dunn G et al., 2004).

It has been suggested that immunotherapy can be a valuable approach for the treatment of pancreatic cancer (Laheru D and Jaffee M, 2005). In fact, lists of candidate PDA-specific proteins have been generated on the basis of their elevated expression at the RNA level (WO 04/55519), or of large-scale proteomic analysis of serum samples and/or pancreatic samples (Bhattacharyya S et al., 2004; Cao D et al., 2005; Ceeconi D et al., 2003; Chen R et al., 2005; Gronborg M et al., 2006; Honda K et al., 2005; Koomen J et al., 2005; Rodriguez J et al., 2005; Shen J et al., 2004, Rosty C and Goggins M, 2005; Sinha P et al., 1999; Yu Y et al., 2005). Candidate proteins for PDA diagnosis in sera are Fibrinogen gamma (Bloomston M et al., 2006), DEAD-Box protein 48 (Xia Q et al., 2005), MIC-1 (Koopmann et J al., 2004), PTH-related protein (Bouvet M et al., 2001), and calreticulin (Hong S et al., 2004).

However, reliable biomarkers for the early detection of PDA and its differentiation from other pancreatic pathologies or cancers are still needed.

DISCLOSURE OF THE INVENTION

The present Invention is based on the observation that sera from PDA patients, compared to sera from healthy individuals or from individuals affected by other pathologies, contain antibodies directed against specific proteins that are expressed in a cell line originated from pancreatic cancers. The presence of these proteins was confirmed by using purified antibodies specific for such proteins in extracts obtained from normal and PDA pancreatic tissues.

A main object of the present Invention are novel, PDA-associated isoforms of human alpha-enolase (ENOA) that are phosphorylated in at least 3 positions that have also been determined in one of the novel isoforms of alpha-enolase.

A further object of the Invention are antibodies binding these ENOA phosphorylated isoforms and distinguishing them from other ENOA isoforms. The antibodies can be in any appropriate format, such as monoclonal antibodies (in particular human monoclonal antibodies) and antibody fragments.

The proteins that have been defined as PDA-associated in the Invention and antibodies binding them (as well as any other specific means for detecting them), can be used in methods for PDA diagnosis, as well as to identify agents for treating PDA. In particular, the antibody-based detection of the PDA-associated ENOA phosphorylated isoforms in biological samples (such sera or biopsies) obtained from a patient can be used in methods for the diagnosis of PDA, for evaluating the progression of the disease, or for evaluating the effects of drugs for treating PDA.

Further objects of the present Invention are kits for the diagnosis of PDA, for evaluating the progression of the disease, or for evaluating the effects of drugs for treating PDA, the kits comprising at least one of the PDA-associated proteins of the invention and/or of the antibodies binding them.

Other objects of the Invention, including those related to the definition and the use of specific anti-alpha-enolase antibodies in the diagnosis and the treatment of pancreatic cancer are provided in the following description.

DESCRIPTION OF FIGURES

FIG. 2: (A) 2-DE gel prepared using a protein extract from the CF-PAC-1 cell line as an assay for detecting PDA-associated protein expression. The proteins in the cell extract were separated in the gel according to their molecular weight and pI and revealed using silver staining. The position of spots present in Western Blot with PDA sera, and not with control sera, are indicated (the name of the specific protein corresponding to each number is listed in Table I). (B) Histograms representing the percentage of sera from patients (the number of them in each group is indicated as n) that are affected by chronic pancreatitis (CP) or by PDA at different stages (II, III, IV) that contain antibodies recognizing the indicated PDA-associated proteins. The full name of the proteins corresponding to the acronyms is indicated in Table I.

FIG. 3: Alignment of the human alpha-enolase (ENOA; SWISSPROT Acc. No. P06733; SEQ ID NO: 1) and human gamma enolase (ENOG SWISSPROT Acc. No. P09104; SEQ ID NO: 2) protein sequences (the amino acids that are identical in the two proteins are indicated with ":", while those only conserved are indicated with "."). The sequences of the peptides that have been identified by Mass Spectrometry in the 2-DE gel spots and used to assign ENOA isoforms to such spots are underlined.

FIG. 4: Position of phosphorylation sites (bold, underlined) in the protein sequence of human alpha-enolase (ENOA; SEQ ID NO: 1) that are predicted by different algorithms and/or identified experimentally (lower case letters below protein sequence; see legend for references). The peptides identified in ENOA as being phosphorylated in ENOA isoform 3 are boxed with a normal line. The peptides identified as being not phosphorylated in ENOA isoform 3 are boxed with a dashed line.

FIG. 5: (A) Detection of six alpha-enolase isoforms (ENOA 1, 2, 3, 4, 5, 6) by different means. Position of ENOA 1/2, and 3 is indicated with the white arrows. (B) Detection of the six alpha-enolase isoforms (1, 2, 3, 4, 5, 6) in protein extracts from a normal pancreatic tissue or from a pancreatic tissue of a PDA patient, that have been transferred on a membrane and then tested by Western Blot, using anti-ENOA as primary antibody. Positions of ENOA 1/2 isoforms are indicated with the white arrows. As a control of the amount of protein loaded on the gel and transferred on the membrane, the membrane was probed with rabbit polyclonal anti-human actin antibody (dilution 1:10000; Sigma Chemical Co.).

DETAILED DESCRIPTION OF THE INVENTION

The combined use of biochemical and proteomic technologies may allow the identification and the evaluation of individual proteins present in disease-related biological samples. In the present case, this type of analysis was initially directed to a cancer (PDA) and made use of two sources of disease-associated molecules: a cell line (CF-PAC-1) derived from human Pancreatic Ductal Adenocarcinoma (PDA) and sera obtained from a large panel of PDA patients, potentially containing antibodies associated to PDA oncogenesis and/or progression.

Figure 1:
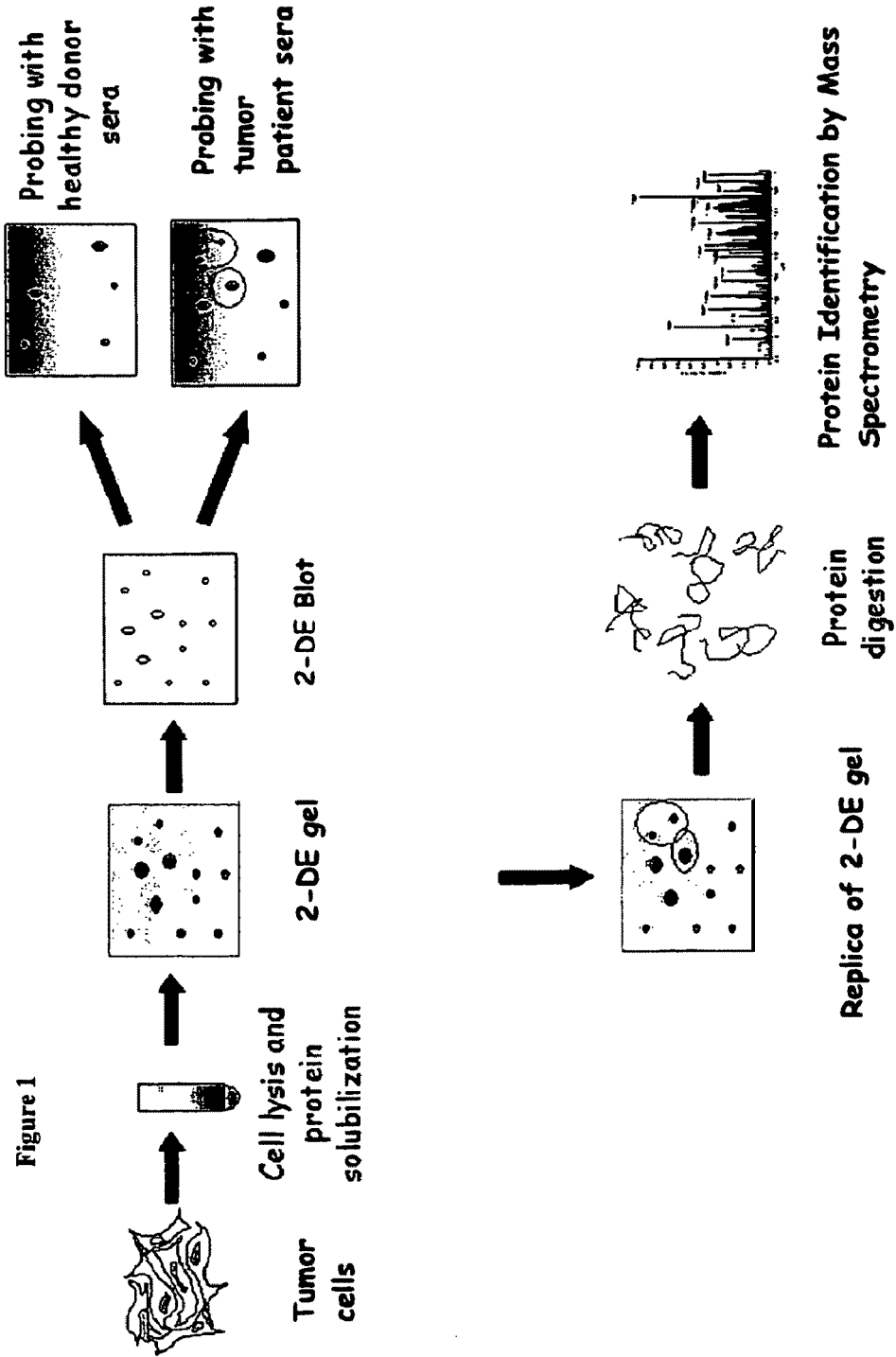
FIG. 1: Schematic representation of the SERPA method applied for characterizing PDA-associated protein antigens and antibodies using CF-PAC-1 cells (tumor cells) and sera from PDA (tumor) patients or control (healthy) donors.

The profile of immunoreactive proteins detected in the CF-PAC-1 extracts by the Western blot analysis of these sera was compared to that obtained using sera from different control populations (healthy subjects, non-PDA tumor patients, chronic pancreatitis patients) in order to establish candidate PDA-associated antibodies and related antigens in the CF-PAC-1 proteome (FIG. 1).

Antibodies to a restricted number of proteins, having distinct known biological activities (including metabolic enzymes and cytoskeletal proteins), were found to be selectively present in sera from PDA patients, suggesting that these proteins are PDA-associated and induce an in vivo antibody response in PDA patients, and not in healthy subjects or in non-PDA cancer patients.

The proteins and antibodies that have been defined as PDA-associated in the Invention (and any other specific means for detecting them), can be used in methods for PDA diagnosis, as well as to identify agents for treating PDA.

The panel of PDA-associated human proteins (comprising alpha-enolase, triosephosphate isomerase, retinal dehydrogenase-1, glucose-6-phosphate-1-dehydrogenase, elongation factor Tu, and isocitrate dehydrogenase, keratin type I cytoskeletal 10, Cofilin 1; FIG. 2B and Table I) has been defined, using the 2-DE and Mass Spectrometry technologies for protein separation and analysis, as the antigens for antibodies specifically present in PDA sera. Moreover, purified antibodies against these antigens confirmed their differential expression, and therefore the usefulness of any protein-based means for detecting them (including sera, fully or partially purified antibodies, polyclonal antibody preparations, and peptides) for the early diagnosis of PDA and for evaluating the progression of this cancer in patients.

These proteins they can be used, each separately or in combination, as biomarkers for the early diagnosis of PDA and for evaluating the progression of this cancer in patients. Amongst these biomarkers, ENOA 1/2 (alpha-enolase isoform 1 and isoform 2) and COF1 (Cofilin 1), as identified by means of 2-DE and Western blot, appear to be the most reliably PDA-associated protein antigens.

As shown in the examples, antibodies binding such PDA-associated antigens can be used for the scopes listed above. Thus, methods comprising the detection of such antigens and/or antibodies in a biological sample (such sera, biopsies, or cell/tissue protein extracts) allow the early diagnosis of PDA and the evaluation the PDA progression in patients.

The characterization of the PDA-associated antigens, except in one case described below, was not extended to the definition of any post-translational modification in the PDA-associated proteins. The data suggest that any antibody or peptic specifically binding either an epitope common to all isoforms of a given antigen (as the purified antibodies used for Table I, right column) or only to the isoform(s) containing the PDA-associated post-translational modification (as those present in the sera of PDA patients and measured during PDA progression; see FIG. 2B), can be used for establishing a PDA diagnosis and progression.

Given the interest in providing novel therapeutic compounds for treating PDA, the methods comprising the detection of PDA-associated antigens and antibodies (as well as of their binding properties) in biological samples can also be used for evaluating candidate drugs for treating PDA. This approach can be applied in assays in which the presence of PDA-associated proteins and/or antibodies can be compared, as shown in the examples with ENOA isoforms (ENOA 1/2).

Changes in these properties, that can be established using the biochemical and proteomic technologies described in the examples and in the literature, and that follows the exposure to a candidate compound, may be indicative of the biological pathway leading to PDA oncogenesis and metastasis. For examples, it is possible to verify the PDA-specific activity of a compound by detecting the disappearance of primary antibodies against the PDA-associated antigens in sera of patients or animal models, as well as the reduction in the number of spots by Western blot in cell extracts using antigen-specific antibodies.

The candidate compounds can be directed to any potential PDA therapeutic target, including those defined in the Invention as PDA-associated proteins (such as COF1 or ENOA 1/2). For example the compounds can be in the form of antibodies binding them (in general or only specific isoforms), or of small molecules altering their expression or post-translational modification by modulating the activity of enzymes modifying them. Moreover, it was found that antibodies binding human alpha-enolase, such as a murine monoclonal antibody, inhibit the in vitro growth and proliferation of transformed cell lines of pancreatic origin presenting six alpha-enolase isoforms (i.e. including ENOA 1/2, as detected using the sera of PDA patients in Western Blot). This inhibitory effect on the in vitro growth and proliferation was observed as well for a transformed cell line of non-pancreatic origin presenting such six alpha-enolase isoforms, but not on one presenting only three, non-phosphorylated these isoforms (Example 3; FIG. 5B; Table IV), suggesting the possibility of using anti-ENOA antibodies for the treatment of PDA.

Such potential therapeutic properties can be then evaluated in any of the proliferation assays for pancreatic cells making use of cell lines or animal models and already tested to verify the effect of different compounds, such as peptides, peptide analogs and small molecules affecting signal transduction (Baker C et al., 2002; Bauer T et al., 2005; Bruns C et al., 2000; Lee L et al., 2002; Levitzki A and Mishani E, 2006; Qin Y et al., 1995; Yezhelyev M et al., 2004; Rubio-Viqueira B et al., 2006). Moreover, the possibility of using combinations of compounds targeting different molecular targets for treating pancreatic cancers more efficient has been demonstrated. For example, the administration of a chemotherapeutic reagent together with inhibitors of kinases specific for cell membrane receptors provided the inhibition of experimental human pancreatic cancer growth and significant prolongation of survival in an animal model (Yokoi N et al., 2005). Alternatively, it has been described that, when two or more antibodies directed to viral or human target are combined in a pharmaceutical composition, the resulting composition may show an improved therapeutic and/or diagnostic efficacy due not only to an additive effect but also a synergic effect. (Logtenberg T, 2007).

A pharmaceutical composition comprising antibodies against the PDA-associated proteins (such as ENOA 1/2) can be administered for therapeutic and diagnostic purpose in humans. Thus, methods for the treatment or the diagnosis of PDA can comprise the administration of pharmaceutical compositions comprising antibodies against the PDA-associated proteins (such as ENOA 1/2).

The compositions may include common pharmaceutical excipients and can be administered in single or multiple dosages and/or using appropriate devices, through different routes: intramuscularly, intravenously, subcutaneously, topically, mucosally, in non-/biodegradable matrix materials, or using particulate drug delivery systems. In particular, the composition should allow the effective administration to the pancreas, or to any other tissues where the PDA-associated proteins can be present.

A pharmaceutical composition should provide a therapeutically or prophylactically effective amount of the compound to the subject that allows the compound to exert its activity for a sufficient period of time. The desired effect is to improve the status of the PDA patient by controlling PDA growth and proliferation, and by reducing at least some of the clinical manifestations of PDA. For example, the composition should be administered at an effective amount from about 0.005 to about 50 mg/kg/body weight, depending on the route of administration and the status of the individual.

In the case of compositions having diagnostic uses, the compound should be detected using technologies commonly established in the clinical and research laboratories for detecting virus in biological samples (e.g. ELISA or other serological assays), or, when administered to a subject in vivo, at least 1, 2, 5, 10, 24, or more hours after administration. The detection of PDA-associated proteins and/or antibodies can be performed, using the PDA-associated proteins and/or antibodies of the invention, following or in combination to the known means and procedures that have been established for diagnosing PDA.

The clinical development and use for PDA therapy and/or diagnosis should be based on the characterization of the antibody pharmacokinetics and pharmacodynamics (Lobo E et al., 2004), the data preclinical and clinical safety (Tabrizi M and Riskos L, 2007), and the compliancy to international requirements for the production and quality control of monoclonal antibodies for therapeutic and in vivo diagnostic use in humans (Harris R et al. 2004).

Kits for PDA diagnosis in a patient may comprise one or more of the PDA-associated proteins and/or antibodies defined above, and any other compound enabling their detection, as defined in the present Invention. These kits can comprise un-/labelled antigens, antibodies, or substrates that are modified following the interaction with such antigen (for examples, in the case of those identified as having enzymatic activities).

Amongst the targets of the humoral response to PDA, of particular interest is the finding that novel, phosphorylated isoforms of alpha-enolase are recognized by PDA sera. The novel isoforms of human alpha-enolase (ENOA) are phosphorylated in at least three positions, and a total of seven phosphorylation sites have been identified (FIG. 4). The importance of this finding is corroborated by the specific detection of two highly phosphorylated ENOA isoforms (ENOA 1/2) using sera obtained from PDA patients or in pancreatic tissues obtained from PDA patients (FIGS. 2B, 5 and 6; Table I and II). PDA patients present antibodies that specifically bind the highly phosphorylated ENOA isoforms of the Invention.

The examples show that, even though several positions in the ENOA sequence can be phosphorylated, a precise combination of Threonine, Serine, and Tyrosine residues is actually phosphorylated, in both cell lines and PDA tissues, and detected by human antibodies produced by PDA patients. In particular, phosphorylation in Threonine 55, Tyrosine 57, Tyrosine 200, Tyrosine 236, Threonine 237, Tyrosine 257, and Serine 419 is present in the ENOA isoform 3 which shows, as ENOA 1/2, a profile of protein phosphorylation that is altered by the treatments with phosphatases. Similar changes in the protein phosphorylation can be used for diagnosing PDA and for evaluating the progression of the disease using biological samples obtained from a patient.

In alternative to full ENOA 1/2 isoforms, it can be useful to generate ENOA-derived single peptides, protein sequences comprising them, or libraries and combinations thereof, that present the same phosphorylated residues of ENOA 1/2, such as those identified in FIG. 4 (see boxed sequences). Methods for generating and using such phosphorylated protein and peptides are disclosed in the literature (Conrads T et al., 2002; U.S. Pat. No. 5,763,164; WO 97/30097).

The number and the effect of post-translational modifications in the alpha-enolase isoforms (in particular ENOA 1/2) can be further confirmed by known technologies (Kalume D et al., 2003; Machida K et al., 2003; Mann M et al., 2002; Rush J et al., 2005; Molina H et al., 2007; Schmelzle K and White F, 2006; Wu J et al., 2005) in PDA-associated and control samples. Additional phosphorylations and/or modifications known for ENOA (Table III) may be present in ENOA 1/2 and relevant for the antigenicity and the biological activity of these isoforms, as well as for their detection by isoform-specific antibodies. Post-translational modification associated to specific stages/types of disease can be detected by several means including direct protein analysis or antibodies distinguishing isoforms having specific modifications, as shown for other proteins (Edberg D et al., 2005; Mandell J, 2003).

Antibodies, in particular monoclonal antibodies, that are defined by the means of their binding to protein isoforms differentially expressed in non-/PDA protein extracts by 2-DE and Western Blot can be used in the treatment of cancers having a similar profile in 2-DE and Western Blot. Thus, antibodies binding alpha-enolase (in general, or the specific phosphorylated isoforms in particular) can be used in the preparation of pharmaceutical compositions for PDA treatment and in methods for the therapeutic treatment of PDA patients, or of cancer patients that present a similar expression profile for alpha-enolase (i.e. expressing the novel isoforms of human alpha-enolase of the Invention that are phosphorylated in at least 3 positions).

Antibodies can be used for the detection or the treatment of cancers (such as PDA) that are characterized by the presence in serum of the patients of phosphorylated alpha-enolase isoforms. These antibodies can be generated by applying any of the known technologies for identifying, characterizing, and producing antibody of diagnostic or therapeutic interest (Jain M et al., 2007; Laffly E and Sodoyer R, 2005). The antibody can be generated in any protein format for functional antibodies, as full antibodies (such a monoclonal antibodies, in particular a human or humanized monoclonal antibody), antibody fragments, antigen-binding proteins, and other engineered antibody-based fusion proteins and peptides, that are described in the literature under different names such as Scfv (single-chain fragment variable), Fab (variable heavy/light chain heterodimer), diabody, isolated heavy or light chains, peptabodies, or bispecific antibodies.

The antibodies of the invention may be improved with the conjugation (using chemical linkers or polymers) or the fusion to a therapeutic, stabilizing, labelling, or diagnostic agents. Examples of these agents are detectable label molecule (e.g. a radioisotope, a fluorescent compound, a toxin, a metal atom, a chemiluminescent compound, a bioluminescent compound, biotin, an enzyme substrate, or an enzyme) that can be bound. The ENOA-specific activity may also be improved by the fusion with another therapeutic protein, such as a protein or a polymer altering the metabolism and/or the stability in diagnostic or therapeutic applications.

Means for choosing and designing protein moieties, ligands, and appropriate linkers, as well as methods and strategies for the construction, purification, detection and use of fusion proteins are provided in the literature (Nilsson et al., 1997; "Applications Of Chimeric Genes And Hybrid Proteins" Methods Enzymol. Vol. 326-328, Academic Press, 2000; WO 01/77137) and are commonly available in clinical and research laboratories. For example, the fusion protein may contain sequences recognized by commercial antibodies (including tags such as polyhistidine, FLAG, c-Myc, or HA tags) that can facilitate the in vivo and/or in vitro identification of the fusion protein, or its purification. Other protein sequences can be easily identified by direct fluorescence analysis (as in the case of Green Fluorescent Protein), or by specific substrates or enzymes (using proteolytic sites, for example).

The antibodies recognizing the PDA-specific protein sequences (such as ENOA 1/2), or any other protein sequences derived from such antibody, can be expressed as a recombinant protein using such vectors for transforming the appropriate host cells which can be prokaryotic or eukaryotic host cells and should allow the secretion of the desired recombinant protein. Methods for producing such proteins include culturing host cells transformed with the expression vectors comprising their coding sequences under conditions suitable for protein expression and recovering the protein from the host cell culture.

The vectors for expression into prokaryotic or eukaryotic host cells, are described in books and reviews on how to clone and produce recombinant proteins, including titles in the series "A Practical Approach" published by Oxford Univ. Press ("DNA Cloning 2: Expression Systems", 1995: "DNA Cloning 4: Mammalian Systems", 1996; "Protein Expression", 1999; "Protein Purification Techniques", 2001). Additional protein sequences can be added in connection to the desired antibody format (Scfv, FAb, antibody fragment, fully human antibody, etc.), or to the insertion, substitution, or elimination of one or more internal amino acids. These technologies can also be used for further structural and functional characterization and optimization of the therapeutic properties of proteins in general, and of antibodies in particular (Kim S et al., 2005).

The invention will now be described by means of the following Examples, which should not be construed as in any way limiting the present invention.

EXAMPLES

Example 1

Detection of PDA-associated Humoral Antigens in the Proteome of CP-PAC-1 Cell Line Materials & Methods Human Sera Sera samples were isolated from venous blood with the informed consent of patients and healthy donors and the approval from the Ethical Committees of the clinical institutions. Samples were stored at −80° C. until use.

Sera was obtained from 70 PDA patients (31 men, 39 women; 32-86 range years; age mean±Standard Deviation: 67±11) were and grouped in different clinical stages according to the classification commonly used (Faria S et al., 2004) and to the UICC (Union International Contre le Cancer) classification as follows: 17 at stage II (no metastasis, moderately differentiated), 17 at stage III (no metastasis, poorly differentiated), and 36 at stage IV (distant metastasis, undifferentiated).

The reactivity of these sera was compared to that of 40 healthy subjects that were used as controls without a prior history of cancer or autoimmune disease (14 men, 26 women; 57-77 range years; age mean±Standard Deviation: 70±7). In addition, the reactivity of these sera was compared to that of 30 non-PDA cancer patients (9 patients with hepatocellular carcinoma, 12 with breast cancer, 8 with colon cancer and 1 with ovarian cancer; 11 men, 19 women; 44-79 range years; age mean±Standard Deviation 66±10) and 15 patients with chronic pancreatitis (9 men, 6 women, 49-76 range years; age mean±Standard Deviation: 59±8).

Age and sex distribution amongst the different groups of patients providing the sera did not show statistically significant differences as evaluated by unpaired 2-tailed Student's t-test. Only in the group of chronic pancreatitis, the age (but not the sex) distribution of these two groups was significantly different, since this disease generally occurs at a younger age (around 44 years, on average) than PDA.

Cell Lines and Preparation of Cell Extracts.

Cells ($10^7$) from the CF-PAC-1 cell line (ECACC Ref. no. 91112501), derived from a Pancreatic Ductal Adenocarcinoma (Schoumacher R et al., 1990) were harvested and washed with Hank's Balanced Salt Solution (Sigma Chemical Co., St. Louis, Mo., USA). The pellets was freeze-dried overnight and stored at −80° C. The pellets were re-suspended in 200 μl of re-hydration buffer [5 M urea, 2 M thiourea, 4% w/v CHAPS (Sigma Chemical Co.), 2%, v/v IPG buffer 3-10 NL(GE Healthcare Bio-Sciences, Uppsala, Sweden), 80 mM DTT (Sigma Chemical Co.)] and a trace of Bromophenol Blue (Sigma Chemical Co.). Protein concentration was measured with the Bradford assay (Bio-Rad Laboratories).

Two-Dimensional Gel Electrophoresis (2-DE)

One hundred μg of protein extract from CF-PAC-1 cell line was loaded by in gel rehydration onto 7 cm IPG strips, (pH 3-10 NL), for analytical and preparative gels. Isoelectric focusing (IEF) was performed on an IPGphor IEF unit system (GE Healthcare Bio-Sciences) with voltage gradient up to 5000 V for a total of 16000 Vh. Prior to SDS-PAGE, the IPG strips were equilibrated for 15 minutes with a solution of Tris/HCl buffer (50 mM; pH 8.8), urea (6 M), glycerol (30% v/v), SDS (2% w/v) and DTT (2% w/v), and then for a further 5 minutes in the same buffer containing iodoacetamide (2.5% w/v) and Bromophenol Blue instead of DTT. For the second-dimension, 7 cm strips were run on small NuPAGE® Novex® 4-12% Bis-Tris Zoom® pre-cast gels (Invitrogen, Groningen, the Netherlands) using Novex X-Cell II™ Mini-cell system (Invitrogen) at a constant 200V and transferred onto a Hybond ECL nitrocellulose membrane (GE Healthcare Bio-Sciences) using Novex X-Cell II™ Blot Module (Invitrogen) or silver stained for mass spectrometry analysis (Shevchenko A et al., 1996).

The pI values of the protein spots were estimated from their position on the 2-DE gel with pH gradient graphs provided by GE Healthcare Bio-Sciences. The molecular weight of the proteins was calculated by comparison with the migration of SeeBlue Plus2 Prestained standards (Invitrogen) of known molecular weight. The 2-DE gel images, were acquired with "ImageScanner" (GE Healthcare Bio-Sciences) and recorded in TIFF format with "ImageMaster Labscan Ver 3.00" software (GE Healthcare Bio-Sciences).

Western Blot Analysis

Membranes were incubated for 15 hours at 4° C. with a blocking buffer consisting of TBS containing 5% nonfat dry milk and then incubated 4 hours with serum (1:200 working dilution in TBS containing 0.05% Tween 20 and 5% nonfat dry milk). After washing the membranes were incubated with horseradish peroxidase (HRP)-conjugated rabbit anti-human immunoglobulin G (IgG) antibody (Santa Cruz Biotechnology) at a 1:1000 dilution for 90 minutes at room temperature.

Alternatively, for Western Blot analysis using purified primary antibodies, the nitrocellulose membranes blotted from 2-DE gels were probed with 1:1000 dilution of antibodies either of mouse origin [such as the monoclonal antibodies anti-enolase 19/12[8] (a subclone of the clone 19/12 characterized in Moscato S et al., 2000), anti-triosephosphateisomerase 1 (Abnova Corporation), anti-Keratin 10 (Chemicon International), anti-elongation factor tu (Abnova Corporation)] or of rabbit origin [such as the polyclonal antibodies anti-aldehyde dehydrogenase 1 (Chemicon International), anti-glucose-6-phosphate1-dehydrogenase (Bethyl laboratories), anti-isocitrate dehydrogenase (Biogenesis Ltd) and anti-cofilin 1 (Cell Signaling), for 1 hour at 25° C. Then, the membranes were incubated for 1 hour with the specific secondary HRP-conjugated goat antibody, either anti-mouse IgG or anti-rabbit IgG (Santa Cruz Biotechnology), according to Manufacturers' instructions.

Western blot analysis of pancreatic tissues was performed using a total of 30-50 mg of fresh frozen tissue that was homogenised (T18 basic UltraTurrax) on ice in 400 μl lysis buffer containing 50 mM TRIS/HCl pH 7.4, 150 mM NaCl, 1% NP40, 1% Triton X-100, 1 mM DTT, 10 μl/ml inhibitory cocktails, 1 mM PMSF (all Sigma Chemical Co.) and 10 μl/ml nuclease mix (GE Healthcare Bio-Sciences). After sonication with an ultrasound sonicator (Hielscher UP200S, 3×40 seconds, amplitude 40%, cycle 0.5), the mix was centrifuged (13000 rpm/min at 4° C. for 30 minutes). Twenty μg of protein extract, contained in the supernatant and measured with the Bradford assay (Bio-Rad Laboratories), was run on a small NuPAGE® Novex® 4-12% Bis-Tris pre-cast gel (Invitrogen), and transferred to a nitrocellulose membrane as described above.

Immunodetection was performed by ECL (Enhanced Chemiluminescence, GE Healthcare Bio-Sciences) and followed by autoradiography on hyperfilm (GE Healthcare Bio-Sciences). Images of developed films were acquired with "ImageScanner" (GE Healthcare Bio-Sciences), recorded in TIFF format with "ImageMaster Labscan Ver 3.00" software (GE Healthcare Bio-Sciences) and analyzed using Image Master 2D Elite version 3.1 software (GE Healthcare Bio-Sciences).

Protein Identification by Mass Spectrometry (MS)

For MS analysis, the spots of interest were excised from preparative 2-DE gels and analysed by Matrix-Assisted Laser Desorption Ionization/Time of Flight (MALDI-TOF) and, when necessary, by Electron Spray Ionization (ESI).

Proteins were de-stained overnight with a solution of 25 mM ammonium bicarbonate and 50% acetonitrile and then digested in gel with trypsin (Promega, Madison, Wis., USA) as previously described (Hellman U et al., 1995). For MALDI-TOF MS, 0.5 μL of each peptide mixture was applied to a target disk and allowed to air dry. Subsequently, 0.5 μL of matrix solution (1% w/v α-cyano-4 hydroxycinnamic acid in 30% acetonitrile, 0.1% TFA) was applied to the dried sample and again allowed to dry. Spectra were obtained using a Bruker Reflex III MALDI-TOF spectrometer. The MS spectra interpretation of protein digests was done by "peptide mass fingerprinting" (PMF) using MS-Fit software (Chamrad D et al, 2004).

For MS/MS experiments, the tryptic peptide mixture was desalted and concentrated in ZipTip$_{C18}$ devices (Millipore). After elution with 60% methanol plus 1% formic acid, 4.5 μl of the tryptic peptide mixture was introduced into a gold-coated borosilicate capillary (Proxeon Biosystems) and analyzed in an LCQ Thermo (ThermoFinnigan) ion trap mass spectrometer fitted with a nano ESI source. The capillary voltage was set to 46 V and spray voltage to 1.8 kV. The most stable signals from the full-scan mass spectrum were trapped and fragmented by low-energy collision-induced dissociation (CID), with normalized collision energy ranging from 22 to 24%.

Some proteins were also identified by LC-MS/MS using a LCQ DECA XP Plus ion trap mass spectrometer (ThermoFinnigan) equipped with an ESI ion source. The chromatographic separations followed by a MS analyzer were run on a C18 column Luna, 150×2.0 mm (Phenomenex), using a Surveyor (autosampler and pump) instrument (ThermoFinnigan) with an injection volume of 10 μL and a flow rate of 200 μl/min.

For all MS/MS data analysis, Bioworks 3.0 (ThermoFinnigan) software was used, and the resulting sequences were compared with the sequences of human proteins present in EBI databases using FASTA software (Johnson R et al., 2005).

Statistical Analysis

All statistics were computed using GraphPad Prism Software. Data are presented as mean±SEM (standard error of mean). A unpaired 2-tailed t test was used for assessing the significance of different protein expression among PDA and normal pancreatic tissues. A 2-sided P value of <0.05 was considered statistically significant.

Results

The proteome of the CF-PAC-1 cell line, often used as a model for PDA-associated protein expression and cell proliferation (Bouvet M et al., 2001; Szepeshazi K et al., 2005), was used to identify the presence of proteins and antibodies that are associated to PDA using sera from PDA patients as source of a primary antibodies.

Protein extracts from this cell line were analyzed by 2-DE, defining a representative two-dimensional map by silver staining. This approach allow separating the proteins contained in this extract as "spots" that can be categorized according to their intensity and position in the 2-DE gel, and for which amount, molecular weight and pI of the proteins can be approximately determined.

The 2-DE gels were transferred onto a membrane in order to be analyzed by Western blot using a panel of sera from either PDA patients or non-PDA patients (including healthy subjects, patients affected by other cancers, and patients affected by chronic pancreatitis). The comparison amongst the different maps of spots (and between the silver staining image and the corresponding Western Blot image of the 2-DE gels) leads to the identification of PDA-associated spots that can be further characterized, for example by Mass Spectrometry analysis of the protein fragments extracted from such spots using enzymes that digest proteins in a controlled manner (FIG. 1).

Using this approach, ten spots were selected and further characterized as being recognized uniquely by serum antibodies from PDA patients (FIG. 2A). The analysis was restricted to human IgG antibodies since the secondary antibody that has been used is specific for this isotype. The ten spots were excised from preparative gels and analyzed by MALDI-TOF MS to identify which human proteins they correspond. Using this approach, nine different proteins were identified as PDA-associated antigens. Two pairs of spots corresponded to isoforms of the same protein and one spot contained sequences belonging to two different proteins not sufficiently separated by 2-DE. All of these spots were absent or almost undetectable in Western Blot performed using control sera. Primary antibodies binding one or more of the proteins in these spots were identified in a significant percentage of sera obtained from PDA patients (Table I).

Amongst these PDA-associated antigenic proteins, a distinction can be made between two categories of proteins, according to the type of biological activities for which they are identified in the literature. A first group of proteins comprises metabolic enzymes: alpha-enolase (present in two spots, each corresponding to a specific isoform), triosephosphate isomerase (present in two spots, each corresponding to a specific isoform), retinal dehydrogenase-1, glucose-6-phosphate-1-dehydrogenase, elongation factor Tu, and isocitrate dehydrogenase. A second group of proteins have been mostly characterized as cytoskeletal proteins: keratin type I cytoskeletal 10, and Cofilin 1.

In addition to the findings obtained using CF-PAC-1 cells and human sera, pancreatic extracts that have been obtained from healthy and PDA subjects, were compared in Western Blot using purified antibodies against these proteins (and not human sera) as primary antibody. This analysis allows for a quantification of total amount of a protein (and not restricted to an isoform), but it shows that these proteins were overexpressed, to various degrees, in the pancreatic tissues obtained from biopsies of PDA patients (Table I).

The diagnostic value of these proteins (and of the presence of specific antibodies against them in PDA sera) has been further evaluated by distinguishing the presence of the spots for each protein amongst PDA sera obtained from patients grouped according to the stage of the disease, and using sera from patients with chronic pancreatitis as controls.

The Western blot analysis showed that the presence and amount of autoantibodies against the different proteins is not uniformly distributed amongst patients at different PDA stages (FIG. 2B). Autoantibodies against most of the proteins were absent in the control sera, while the frequency of PDA sera containing them slightly increases in patients at stage II PDA for most of the proteins (below 25%) with the notable exception of ENOA 1/2. These frequencies in the profile of autoantibodies production is confirmed in most advanced stages, where again the autoantibodies against alpha-enolase isoforms are the most interesting, given the constant increase in the frequency at stage III and stage IV PDA.

Conclusions

A serological-based approach that combined 2-DE expression profiling of a human pancreatic tumor cell line (CF-PAC-1) and Western Blot analysis (using, as primary antibodies, human IgG in the serum from patients with PDA) allowed the identification of a restricted number of human proteins and of their isoforms against which PDA patients produce a specific humoral response. With only one exception (AL1A1), the expression of these proteins was up-regulated in PDA biopsies. Moreover, the production of antibodies against these PDA-associated proteins seems, at least for some antigens, to significantly increase in advanced stages of the disease.

These results demonstrate the suitability of serological approaches in identifying potential markers for early PDA diagnosis that are, in this case, mostly intracellular. The mechanism whereby the immune system reacts to intracellular proteins is unclear, but may be dependent on the unique environment created by the tumor that can alter localization of intracellular enzymes in tumor cells.

Cofilin 1 (COF1) plays a role in actin remodelling, motility and cancer as an actin depolymerizing enzyme involved in invadopodium formation (Yamaguchi H et al., 2005) and may be required for tumor cell directionality in response to chemotactic or growth-factor stimulation (Mouneimne G et al., 2004). Overexpression of COF1 has been previously observed in association with PDA animal models (Cecconi D et al., 2003; Sinha P et al., 1999).

Alpha-enolase is a highly conserved metabolic enzyme having multiple properties and detected in different contexts (Pancholi V, 2001; Piast M et al., 2005; Terrier B et al., 2007).

It can be expressed on the cell surface as a plasminogen receptor (Lopez-Alemany R et al., 2003) and recognized by B cells, potentially acting as a B cell activator (Babu J et al., 2002). Two isoforms have been detected in pancreatic adenocarcinoma but without describing their molecular properties in terms of post-translational modifications (Shen J et al., 2004).

Autoantibodies against alpha-enolase, existing as a single isoform or in multiple isoforms (but without evidence of the specific expression of ENOA phosphorylated isoforms), have been identified in many different biological and disease models, such as in cancer-associated retinopathy (Adamus G et al., 1998; Adamus G et al., 1996), non-small lung cancer and other non-pancreatic cancers (WO 07/072219; US20070172487: He P et al., 2007), biliary cirrhosis (Akisawa N et al., 1997), encephalopathies (Fujii A et al., 2005), and autoimmune diseases (Ballot E et al., 2003; Bogdanos D et al., 2004; Gitlits V et al., 2001). The properties of alpha-enolase and of alpha-enolase specific antibodies or autoantibodies have been studied using phage display (Arza B et al., 1997; Kemp E et al., 2002) or peptides (Adamus G et al., 1998; Sato N et al., 2000; Walter M et al., 1995; Fujii A et al., 2005).

The present results demonstrate that specific alpha-enolase isoforms and antibodies for detecting them are a particularly useful tool for PDA diagnosis, given the frequency and the specific production of autoantibodies against two specific isoforms of this protein (ENOA 1/2) in the sera from PDA patients (Table I and FIG. 2B). The antibodies can be specific for an epitope common to all, or most, isoforms (as the purified antibodies used in the experiment) or an epitope distinguishing the PDA-associated isoforms from the others (as those present in the PDA sera). Moreover, the progression of PDA from stage II to IV is characterized by a highly significant enhancement of the production of autoantibodies against ENOA 1/2, suggesting a direct correlation with tumor size and growth ability.

A more detailed analysis of such isoforms is important not only for establishing the predictive value of the autoantibodies for PDA diagnosis, but also to have a deeper understanding of the molecular mechanisms linking them to PDA and to possible therapeutic approaches against this cancer.

Example 2

Analysis of Alpha-Enolase Isoforms Detected by Autoantibodies in CF-PAC-1 Cells

Materials & Methods

MS Analysis

Spots were excised from preparative 2-DE gels and analysed by Matrix-Assisted Laser Desorption Ionization/Time of Flight (MALDI-TOF). Proteins were de-stained overnight with a solution of 0.025 mol/L ammonium bicarbonate and 50% acetonitrile and then digested in gel with trypsin (Promega, Madison, Wis.) as previously described (Hellman U et al., 1995). For MALDI-TOF MS, 0.5 µL of each peptide mixture was applied to a target disk and allowed to air dry. Subsequently, 0.5 µL of matrix solution (1% w/v α-cyano-4 hydroxycinnamic acid in 30% acetonitrile, 0.1% TFA) was applied to the dried sample and again allowed to dry. Spectra were obtained using a Bruker Reflex III MALDI-TOF spectrometer (Bremen, Germany). The MS spectra interpretation of protein digests was done by "peptide mass fingerprinting" (PMF) using MS-Fit software.

Phosphorylation Analysis

The analysis of human alpha-enolase protein sequence was performed using the following software available by Internet: NetPhos [ (B lorn N et al., 1999)], NetPhosK [(Blom N et al., 2004)], dbPTM [(Lee T et al., 2006)], PPSP [(Xue Y et al., 2006)], and GPS [(Xue Y et al., 2005)].

Phosphatase treatment was performed using λ PPasc (New England Biolabs Inc.) as described (Yamagata A et al., 2002) with the following modifications. Pelleted CF-PAC-1 cells ($30 \times 10^6$) were resuspended for 15 hours in 1 ml of lysis buffer (1% w/v NP-40, 1% w/v SDS, 50 mM Tris pH 7.6, and 150 mM NaCl protease inhibitor cocktail). The lysate (120 µl, corresponding to 2 mg of protein) was brought to a final volume of 1240 µl with deionized water, then 20 µl of 20 mM $MnCl_2$ solution and 20 µl of λPPase buffer were added. After each addition, the solution was gently mixed. The mixture was divided into aliquots, and 600 units of λPPase was added to an aliquot. After mixing, aliquots were incubated for 15 hours at 30° C. Proteins were acetone and chloroform precipitated and used for 2-DE analysis (see Example 1).

Dye-based detection of phosphoproteins was performed in 2-DE gels using ProQ phosphoprotein fluorescence dye (Molecular Probes) and with Sypro Ruby stain (Bio-Rad) for detection of total proteins as described by Manufacturer's instruction and in the literature (Wu J et al., 2005). Briefly, following 2-DE, Pro-Q stain was performed by first fixing the gels in 50% methanol/10% Acetic acid 30 min. The gel was then washed with distilled water and subjected to Pro-Q Diamond phosphoprotein stain for 4 hours. Destaining was conducted with successive washes of 50 mM sodium acetate, pH 4.0 containing 20% acetonitrile prior to the staining with Sypro Ruby fluorescence dye (overnight).

Analysis of the Expression of ENOA Isoforms in Pancreatic Tissues from Biopsies

Pancreatic tissues obtained from biopsies of either healthy individuals or of PDA patients (Stage II) were homogenised (T18 basic UltraTurrax, IKA,) on ice, in 400 µl lysis buffer containing 5 mol/L urea, 2 mol/L thiourea, 4% w/v CHAPS, 2%, v/v IPG buffer nonlinear pH 3-10, 0.08 mol/L dithiothreitol (DTT), 10 µL/mL nuclease mix and a trace of Bromophenol Blue. After sonication with an ultrasound sonicator (Hielscher UP200S, 3×40 s, amplitude 40%, cycle 0.5 Hielscher Ultrasonics GmbH), the mix was centrifuged (13000 rpm, 30 minutes at 4° C.) with the protein solution contained in the supernatant.

Protein concentration was measured with the Bradford assay. Thirty µg of protein extract was run on a small NuPAGE® Novex® 4-12% Bis-Tris pre-cast gel, transferred to a nitrocellulose membrane, incubated overnight at 4° C. with the anti-alpha-enolase monoclonal antibody 19/12[8] (Moscato S et al., 2000) and revealed in Western Blot as described in Example 1.

Production of Recombinant Histidin-tagged ENOA (rENOA).

The recombinant protein was purified from *E. coli* cells trasfected with a plasmid encoding the sequence of human ENOA (missing only the first nine amino acids) fused to an Histidin tag. Briefly, bacterial cells were harvested from 1 liter culture by centrifugation and pellets were resuspended in 20 ml of Native Binding Buffer (NBB, 20 mM sodium phosphate and 500 mM sodium chloride, pH 7.8) with the addition of lysozyme (100 µg/ml) and sarcosyl 0.7%. The suspension was slowly rocked for 15 minutes at 4° C. The cell lysate was sonicated on ice with ten 40-second pulses at high intensity. The lysate was centrifuged at 10000 rpm for 15 minutes at 4° C. to pellet the insoluble fraction, which was resuspended in 10 ml of guanidinium lysis buffer (6 M guanidine hydrochloride, 20 mM sodium phosphate, 500 mM sodium chloride, pH 7.8), enriched with protease inhibitors, for 10 minutes at room temperature. The lysate was added to the equilibrated column (Ni-NTA agarose column, Invitrogen) to allow binding to the resin for 30 minutes at 4° C. using gentle rotation. The resin was washed twice with NBB and twice with Native Wash buffer (NWB; NBB at pH 6.0) followed. The elution was performed with 10 ml of imidazole elution buffer (350 mM pH 6=Production of recombinant Histidin-tagged ENOA (rENOA). The eluted fractions were dialysed in sterile water, then lyophilised and resuspended in sterile pyrogen-free Dulbecco's phosphate buffered solution (DPBS, Sigma). Aliquots were stored at −20° C. The endotoxin level was less than 0.03 EU/ml in the *Limulus* Amebocyte Lysate assay (Pyrogent; BioWhittaker).

Analysis of the Expression of ENOA Isoforms in CF-PAC-1 Using Patient Sera and Western Blot CF-PAC-1 2-DE gels were electrotransferred onto a Hybond ECL nitrocellulose membrane (GE Healthcare) as described above. After blocking for 1 h with TBS containing 5% nonfat dry milk, blots were incubated with pool of three sera of ENOA 1/2+ patients (diluted 1:100 in TBS) in different conditions.

In a series of experiments, the pool of sera was first incubated for 15 hours at 4° C. on a rocker with 20 µg/ml of recombinant alpha-enolase (rENOA) before performing the incubation with the membrane. In another series of experiments, the membrane were first incubated with 2 ml of PBS containing 600 units of λPPase, 40 µl of 20 mM MnCl2 solution and 40 µl of λPPase buffer for 15 hours at 30° C. Membranes were blocked again for 1 hour, washed three times for 15 minutes with TTBS and incubated with a pool the sera (dilution 1:100).

The binding of antibodies in the sera to ENOA isoforms was revealed using labeled anti-human antibodies in Western Blot as described in Example 1. As a control of the quantity of immobilized ENOA, the membrane were reprobed with the murine monoclonal antibodies anti-enolase 19/12[8] (see example 1).

Results

After demonstrating that two isoforms of human alpha-enolase are specifically detected by antibodies in the sera of PDA patients, the features characterizing such isoforms (and any other isoform of this protein that are present in CF-PAC-1 cells) was performed using different approaches.

The comparison of the Western blot obtained using the purified antibody against alpha-enolase or the sera of different PDA patients, the silver staining of 2-DE gels, and the Mass Spectrometry analysis showed that 4 additional spots, corresponding to additional alpha-enolase isoforms not associated to PDA, were present in 2-DE gels, having similar molecular weight but experimental pI values lower than ENOA 1/2 (Table II). These evidences were obtained using CF-PAC-1 or MiaPaCa-2 cell extracts in 2-DE gel analysis.

The peptides obtained from such spots were identical to fragments of ENOA (and clearly distinct from the highly similar, human gamma-enolase; FIG. 3), confirming the Western blot evidence that the spots should correspond to ENOA isoforms, wherein only ENOA 1/2 are PDA-associated. Post-translational modifications are features that often distinguish one isoform from another. The preliminary analysis seemed to exclude glycosylation (given the limited changes in the molecular weight) and suggested phosphorylation modifications (given the pI decrease).

The sequence of human alpha-enolase contains several Tyrosine, Serine, and Threonine residues that are potential targets for phosphorylation by different kinases. This hypothesis was tested by exposing the protein extract to a broadly active phosphatase prior to the 2-DE separation to see if there was any change in the intensity of the spots detected using a phosphorylation-independent antibody, as shown in the literature for other proteins (Kumar Y et al., 2004). In fact, the intensity of the ENOA spots corresponding to the most acidic isoforms (that is the PDA-associated ENOA 1/2 and the ENOA isoform 3; Table II) was clearly reduced in phosphatase pre-treated CF-PAC-1 cell extracts. Moreover, Mass Spectrometry analysis of ENOA isoform 3 (more abundant than ENOA 1/2) showed that residues 55, 57, 200, 236, 237, 257, and 419 are phosphorylated in this isoform (FIG. 4).

Previous reports on in vivo or in vitro phosphorylation of alpha-enolase (Cooper J et al., 1984; Eigenbrodt E et al., 1983; Marcus K et al., 2000; Rush J et al., 2005; Stasyk T et al., 2005; Molina H et al., 2007) failed to indicate, in general, that at least three specific residues can be simultaneously phosphorylated, and, in particular, residues 55, 57, 200, 236, 237, 257, and 419 can be found phosphorylated in ENOA isoforms. Moreover, the combination of phosphorylated residues in ENOA isoform 3 was hardly predictable using a software-based analysis of ENOA protein sequence since there is a high number of candidate sites for phosphorylation (FIG. 4). It cannot be excluded that ENOA isoform 3 may have additional phosphorylation sites not detected at this stage of the Mass Spectrometry analysis, but ENOA 1/2 should contain post-translationally modified residues (most likely phosphorylated as well, due to the pI value and the findings obtained using phosphatase) that characterize them from ENOA isoform 3.

Notably, more than one of the peptides obtained from ENOA3 isoform, for which the phosphorylation state was determined and which contains candidate phosphorylation sites, do not show such a modification. For example, Tyrosine 44 specifically identified in the literature as being phosphorylated in an established leukemic T-cell line (Rush J et al., 2005) was not found phosphorylated in ENOA isoform 3. Similarly, residue 57 that has been identified as phosphorylated in combination with residue 63 (Molina H et al., 2007), and not with residue 55, as in ENOA isoform 3 (FIG. 4).

A further analysis of the phosphorylation in the ENOA isoforms detected using both PDA sera and ENOA-specific antibodies was performed by comparing the images obtained in Western Blot with those obtained using dyes staining total proteins in the 2-DE gel (silver staining or Sypro Ruby) or specific for phosphoproteins (Pro-Q Diamond). This analysis confirmed that only ENOA 1/2 and 3 are phosphorylated in CF-PAC-1 cells (FIG. 5A; Table II).

The ENOA expression was also tested by Western Blot on tissues obtained from surgically treated PDA patients (Stage II; n=7) and normal pancreatic tissue (n=1), using an anti-enolase antibody binding to a specific epitope common to all the six isoforms that are detected in the sera of PDA patients. In six out of seven PDA biopsies, all six ENOA isoform were detected. By contrast, in the normal pancreatic only four isoforms (ENOA 3, 4, 5 and 6) wore clearly detectable (FIG. 5B). So it can be concluded that not only PDA patients produce antibodies against ENOA 1/2, but also that these isoforms are significantly overexpressed in PDA pancreatic tissues.

The reactivity of sera from PDA patients against phosphorylated ENOA was further investigated using CF-PAC-1 cell extracts in 2-DE and Western blot at the scope of understanding if this reactivity is specifically directed to their phosphorylated epitopes. Since PDA patient sera reacted to all six isoforms, they may contain antibodies reacting to either phosphorylated or unphosphorylated epitopes.

Figure 6:
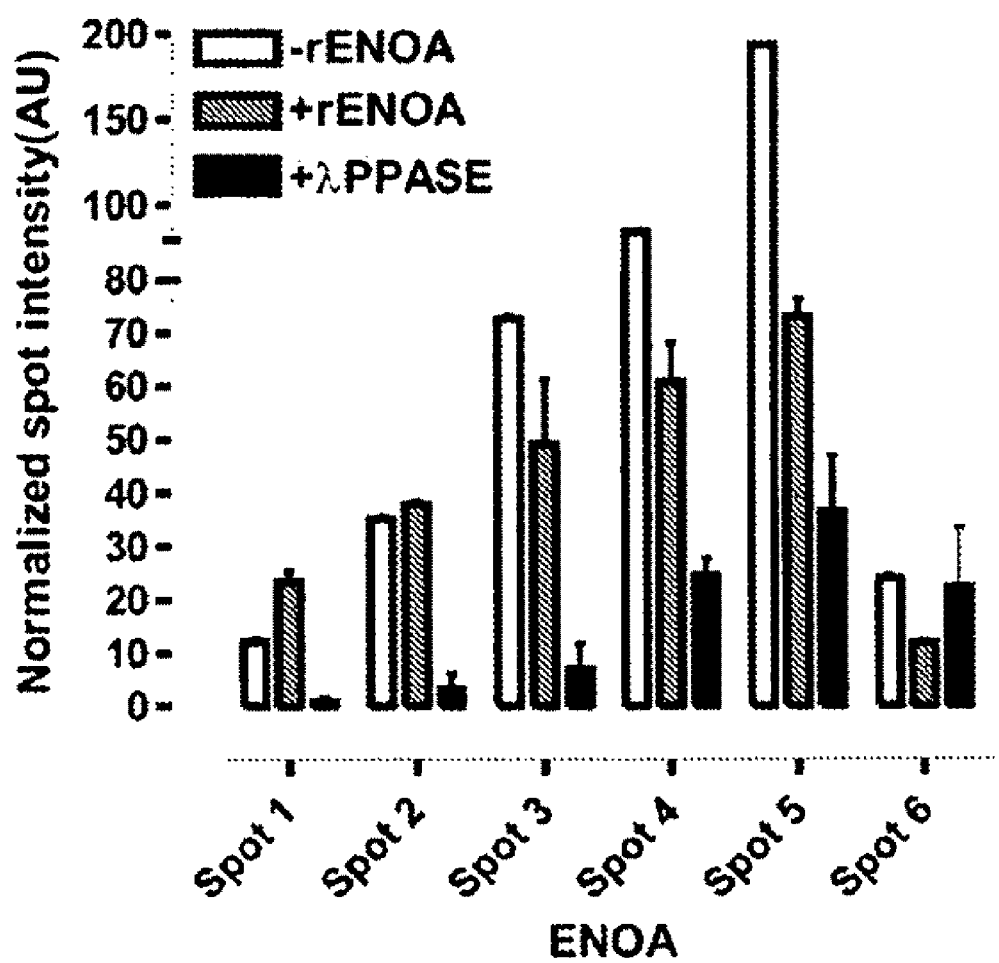
FIG. 6: Detection of the six alpha-enolase isoforms (spot 1, 2, 3, 4, 5, 6) in CF-PAC-1 cell extracts by 2-DE gels and Western Blot, using (as primary antibody) a pool of PDA patient sera with or without pre-adsorption with recombinant human alpha-enolase (+rENOA or −rENOA). Alternatively, the membrane was pre-treated with a phosphatase (+λP-PASE) before performing Western Blot, using (as primary antibody) a pool of PDA patient sera.

In a first series of experiments, the sera were preincubated with recombinant human ENOA, which does not contain phosphorylated residues, to see if exposure to ENOA antigens alter the ability of sera to recognize ENOA isoforms in the reference pancreatic cell line. In fact, the two-DE Western Blot analysis revealed that unphosphorylated ENOA markedly reduced reactivity only to isoforms 3, 4, 5 and 6, without affecting the reactivity to ENOA 1/2 isoforms. This evidence was further confirmed in another series of experiments in which the membrane was pre-incubated with a phosphatase (λPPase) to confirm that patient sera contain antibodies that react specific to phosphorylated ENOA 1/2 isoforms. In the absence of λPPase, the sera recognized all ENOA isoforms, whereas λPPase treatment markedly reduced sera reactivity to ENOA 1/2 (FIG. 6).

As anti-ENOA mAb equally detected all isoforms in treated or untreated membranes, (data not shown), these data demonstrate that antibodies in the sera of PDA patients specifically react to phosphorylated ENOA 1/2 isoforms.

Conclusions

Using different proteomic approaches, multiple isoforms of ENOA and antibodies against them have been identified (Adamus G et al., 1998; Adamus G et al., 1996; Akisawa N et al., 1997; Ballot E et al., 2003; Bryborn M et al., 2005; Lubec C et al., 2003; O'Dwyer D et al., 2002). However, these reports do not provide a clear demonstration of an association between the phosphorylation states and positions to the production of autoantibodies against specific isoforms during PDA progression.

Other articles report changes in the intensity and/or number of alpha-enolase spots that arc detection, for example using patients' sera in Western Blot of 2-DE gels, associated to specific cell treatment (Baty J et al., 2005; Bottalico L et al., 1993; Kanamoto T et al., 2002) or diseases (Bytjalsen I et al., 1999; Clauser K et al., 1995, Nakanishi T et al., 2006; Tanaka Y et al., 2006; US20070172487), suggesting that can be due to post-translational modifications such as phosphorylation.

In other reports, human alpha-enolase is indicated as one of the several proteins overexpressed in PDA samples analyzed by 2-DE gels and confirmed at the level of mRNA and immunocytochemistry, but there is no mention of the specific phosphorylations that characterize isoforms of alpha-enolase associated to PDA (WO04/55548; Shen J et al., 2004; Nakanishi T et al., 2006; Mikuriya K et al., 2007).

Amongst the large number of post-translational modifications detected in alpha-enolase (Table III), phosphorylation has been detected both in vivo and in vitro in old literature (Cooper J et al., 1984; Coussens P et al., 1985; Eigenbrodt E et al., 1983; Golden A et al., 1986). Most recently, two phoshorylated isoforms of alpha-enolase have been detected using 2D-gels, a commercial mouse anti-phosphotyrosine antibody (clone 4G10, cod. 05-321; Biomol) and Mass Spectrometry in human platelets (Marcus K et al., 2000). A single phosphorylated variant of alpha-enolase has been detected in TGFbeta1 treated cells (MCF-7 cell line) using 2D-gels, radiolabeling, and Mass Spectrometry (Stasyk T et al., 2005) or in MIAPaCa cells (a pancreatic cancer cell line) where enolase phosphorylation is decreased following the treatment with flavonoids (Lee L et al., 2002). Moreover, two phosphorylation sites located at the Tyrosine residues (44 and 286; Rush J et al., 2005) or Tyrosine and Serine residues (57 and 63; Molina H et al., 2007).

However, none of these documents has associated PDA with the additional phosphorylation of alpha-enolase isoforms already phosphorylated in at least three positions, and to antibody binding them.

Example 3

Effects of Antibodies Binding to Alpha-Enolase on the Growth and Proliferation of Transformed Cell Lines Expressing Phosphorylated Isoforms of Alpha-enolase Materials & Methods Assay for Proliferation of Cell Lines The in vitro assay of cell proliferation was performed with the indicated cell lines by seeding $2-10\times10^3$ cells/well in 96-well microplates in complete cell culture medium (RPMI-1640 with 10% Fetal Bovine Serum) with or without the anti-alpha-enolase monoclonal antibody 72/1 (Moscato S et al., 2000) or mouse IgG1 isotype matched control monoclonal antibody (R&D Systems) used as a negative control.

After 44 or 68 hours, 20 μl of methyl tetrazolium solution (MTT; 5 mg/ml) was added to each well for a further 4 hours at 37° C. Medium was eliminated and cells were dissolved with DMSO. Plates were read to the spectrophotometer at 540 nanometers.

Results

The effects of an anti-alpha-enolase antibody on the growth of cell lines presenting different profile of alpha-enolase expression, as determined by 2-DE and Western Blot, were tested by measuring the incorporation of MTT, a compound that is incorporated in viable cells and correlates with active cell growth, metabolism and proliferation.

Using an MTT-based colorimetric assay, a significant inhibition of cell proliferation is obtained in the transformed cell lines that express all the six isoforms, independently from their pancreatic or non-pancreatic origin. Using an IgG1 isotype matched control monoclonal antibody or a cell line not expressing the three phosphorylated ENOA isoforms, the effect is minimal (Table IV).

Thus, anti-alpha-enolase antibodies are able to inhibit (at least partially) the growth and the proliferation cell lines having the specific phosphorylation profile of alpha-enolase detected in PDA-associated biological samples (such as sera or tissues from biopsies).

CONCLUSIONS

Even though generally considered as a cytoplasmatic protein, alpha-enolase can be expressed as a biologically active protein on the cell surface (Arza B et al., 1997; Bergman A et al., 1997; Moscato S et al. 2000; Lopez-Alemany R et al., 2003) as well as a soluble factor (Babu J et al., 2002; Demir A et al., 2005).

The in vitro data show that the growth of transformed cell lines is slowed by the binding of antibodies to epitopes present in the alpha-enolase isoforms expressed in the extracellular space (as a cell surface receptor and/or as a soluble protein), only if the cell lines express phosphorylated isoforms of alpha-enolase.

Thus, a monoclonal antibody that binds specifically cells presenting alpha-enolase phosphorylated isoforms can inhibit the proliferation of transformed cell lines. This mechanism for controlling cell proliferation seems present not only in PDA but in other forms of cancers presenting such molecular features, and can be targeted by appropriate monoclonal antibodies for cancer-related therapeutic applications, such as the preparation of medicaments for PDA treatment and methods for the diagnosis and the treatment PDA patients.

TABLE I

Proteins recognized by PDA Patient Sera as Antigens

| Description (SWISSPROT Locus, Accession No.) | Distinct spots (No.)[a] | 2-DE, Western Blot, and Mass Spectrometry analysis of CF-PAC-1 cell extracts | | | Western Blot of pancreatic extracts[b] | |
|---|---|---|---|---|---|---|
| | | Spots that are recognized by the sera of | | | | |
| | | Healthy subjects (%) | Non-PDA patient (%) | PDA patients (%) | Normal | PDA (P value)[c] |
| Alpha-enolase (ENOA_HUMAN, P06733) | 2 (No. 1 and 2) | 0/40 (0%) | 0/30 (0%) | 41/70 (58%) | 13.5 ± 0.2 | 33 ± 7 (<0.05) |
| Triosephosphate isomerase (TPIS_HUMAN, P60174) | 2 (No. 3 and 4) | 0/40 (0%) | 0/30 (0%) | 16/70 (23%) | 15.5 ± 0.6 | 28 ± 3 (<0.05) |
| Keratin, type I cytoskeletal 10 (K1C10_HUMAN, P13645) | 1 (No. 5) | 0/40 (0%) | 0/30 (0%) | 15/70 (21%) | 3.5 ± 0.6 | 33 ± 4 (<0.005) |
| Retinal dehydrogenase 1 (AL1A1_HUMAN, P00352) | 1 (No. 6) | 0/40 (0%) | 0/30 (0%) | 14/70 (20%) | 21.2 ± 0.6 | 18 ± 1 (=0.05) |
| Glucose-6-phosphate 1-dehydrogenase (G6PD_HUMAN, P11413) | 1 (No. 7) | 0/40 (0%) | 0/30 (0%) | 9/70 (13%) | 0.6 ± 0.06 | 17.5 ± 5 (<0.05) |
| Elongation factor Tu (EFTU_HUMAN, P49411) | 1 (No. 8) | 0/40 (0%) | 0/30 (0%) | 8/70 (11%) | 2 ± 0.6 | 32 ± 9 (<0.05) |
| Isocitrate dehydrogenase (IDHC_HUMAN, O75874) | 1 (No. 9) | 0/40 (0%) | 0/30 (0%) | 9/70 (10%) | 3 ± 0.6 | 28 ± 8 (<0.05) |
| Transgelin-2 (TAGL2_HUMAN, P37802) | 1[d] (No. 10) | 0/40 (0%) | 0/30 (0%) | 19/70 (27%) | ND | ND |
| Cofilin 1 (COF1_HUMAN, P23528) | | | | | 9 ± 0.6 | 42 ± 5 (<0.005) |

ND: Not determined
[a]Detected by silver staining and Western Blot in 2-DE gels as PDA-specific (see the position of the corresponding spot numbers in FIG. 1B)
[b]Western blot were performed with antibodies specific for each protein. Intensity of reactive lines are expressed as arbitrary units of normalized line intensity (mean of three experiments ± SEM).
[c]The statistical significance of the normalized line intensity of the selected proteins was assessed by using the paired 2-tailed/test
[d]The proteins colocalize in the same spot.

TABLE II

Identification of ENOA isoforms recognized by PDA patient sera

| | 2-DE and Mass Spectrometry | | | 2-DE and Phosphorylation analysis Intensity of spots in Western blot (% of total intensity) | |
|---|---|---|---|---|---|
| ENOA Spot no. | Mol. Weight (kDa)[a] | pI[b] | Score for Matching Peptides[c] (Sequence coverage, %) | No λ PPase | 600U λ PPase |
| 1 | 49.2 | 6.16 | 290 (18%) | 8.5% | 0% |
| 2 | 49.0 | 6.30 | 365 (24%) | 10.9% | 1.9% |
| 3 | 48.9 | 6.58 | 595 (39%) | 15.1% | 6.2% |
| 4 | 48.9 | 6.80 | 1007 (60%) | 65.5% | 91.9% |
| 5 | 48.9 | 7.26 | 1127 (65%) | | |
| 6 | 48.8 | 7.60 | 449 (27%) | | |

LC-MS/MS analysis
[a]The value for human, non-posttranslationally modified alpha-enolase is 47 kD
[b]The value for human, non-posttranslationally modified alpha-enolase is 7.0
[c]The sum of the ions scores of all the non-duplicate peptides

TABLE III

Selected Literature Describing Post-Translational Modifications Of Alpha-Enolase other then Phosphorylation

| Modification | Reference |
| --- | --- |
| Acetylation | Iwabata H et al., 2005 |
| Citrullination | Kinloch A et al., 2005 |
| D-Asp | Takata T et al., 2006 |
| 4-hydroxynonenal modification | Kapphahn R et al., 2006 |
| Nitration | Casoni F et al., 2005; Kanski J et al., 2005; Shin S et al., 2004 |
| Oxidation | Butterfield et al., 2006; Castegna A et al., 2002; Ishii T and Uchida K, 2004; Perluigi M et al., 2005 |
| Tyrosylation | Avram D et al., 2004 |

TABLE IV

Results of the in vitro Proliferation Assay

| Cell line Origin Deposit No. References | Cell growth inhibition (%) anti-ENOA 48 hours | Control IgG 48 hours | ENOA isoforms (as detected by 2-DE and Western Blot) | | | | | |
| --- | --- | --- | --- | --- | --- | --- | --- | --- |
| | | | 1 | 2 | 3 | 4 | 5 | 6 |
| BxPC-3 Poorly differentiated PDA ECACC No. 93129816 Tan M et al., 1986 | 37%) | 0% | + | + | + | + | + | + |
| CF-PAC-1 Differentiated PDA ECACC No. 91112501 Schoumacher et al., 1990 | 29% | 0%) | + | + | + | + | + | + |
| Mia-Pa-Ca-2 Undifferentiated PDA ECACC No. 85062806 Yunis A et al., 1977 | 38% | 0% | + | + | + | + | + | + |
| U937 Lymphoma cell line ECACC No. 85011440 Fischer D et al 1980 | 38% | 5% | + | + | + | + | + | + |
| MCF-7 Breast adenocarcinoma ECACC N° 86012803 Soule H et al., 1973 | 15% (2%) | 0% (0%) | − | − | − | + | + | + |

REFERENCES

Adamus G et al. (1998). J Autoimmun, 11, 671-7.
Adamus G et al. (1996). Clin Immunol Immunopathol, 78, 120-9.
Akisawa N et al., (1997). J Hepatol, 26, 845-51.
Arza B et al., (1997). Thromb Haemost, 78, 1097-103.
Avram D et al., (2004). Proteomics, 4, 2397-407.
Babu J S et al., (2002). Clin Immunol, 104, 293-304.
Baker C H et al. (2002). Cancer Res, 62, 1996-2003.
Ballot E et al. (2003). Clin Chem, 49, 634-43.
Baty J W et al. (2005). Biochem J, 389, 785-95.
Bauer T W et al. (2005). Cancer Res, 65, 7775-81.
Bhattacharyya S et al. (2004). Neoplasia, 6, 674-86.
Bergman A et al., (1997). FEBS Lett, 417, 17-20.
Blom N et al. (1999). J Mol Biol, 294, 1351-62.
Blom N et al. (2004). Proteomics, 4, 1633-49.
Bloomston M et al. (2006). Cancer Res, 66, 2592-9.
Bogdanos D P et al. (2004). J Autoimmune Dis, 1, 4.
Bottalico L A et al. (1993). Arterioscler Thromb, 13, 264-75.
Bouvet M (2004). Ann Surg Oncol, 11, 637-8.
Bouvet M et al. (2001). J Clin Endocrinol Metab, 86, 310-6.
Brand R. (2001). Cancer J, 7, 287-97.
Bruns C J et al. (2000). Cancer Res, 60, 2926-35.
Bryborn M et al. (2005). Respir Res, 6, 118.
Butterfield D A et al. (2006). Neurobiol Dis, 22, 223-32.
Byrjalsen I et al. (1999). Mol Hum Reprod, 5, 748-56.
Cao D et al. (2005). Mod Pathol, 18, 752-61.
Casoni F et al. (2005). J Biol Chem, 280, 16295-304.
Castegna A et al. (2002). J Neurochem, 82, 1524-32.
Cecconi D et al. (2003). Electrophoresis, 24, 4291-303.
Chamrad D et al., (2004). Proteomics. 4: 619-28.
Chen R et al. (2005). Mol Cell Proteomics, 4, 523-33.
Clauser K et al. (1995). Proc Natl Acad Sci USA, 92, 5072-6.
Cohen S and Meropol N (2002). Int J Gastrointest Cancer, 32, 91-106.
Conrads T et al. (2002). Biochem Biophys Res Commun, 290, 885-90.
Cooper J et al. (1984). J Biol Chem, 259, 7835-41.
Coussens P et al. (1985). Mol Cell Biol, 5, 2753-63.
Demir A et al., (2005) Cell Tissue Res, 322, 299-311.
Drake C et al. (2006). Adv Immunol, 90, 51-81.
Dunn G et al. (2004). Immunity, 21, 137-48.
Edberg D et al. (2005). J Biol Chem, 280, 8961-73.
Eigenbrodt E et al. (1983). Embo J, 2, 1565-70.
Faria S et al. (2004). Semin Roentgenol, 39, 397-411.
Fischer D et al., (1980). J. Immunol. 125:463-5.
Fujii A et al., (2005). J. Neuroimm. 162: 130-6.
Gitlits V M et al. (2001). J Investig Med, 49, 138-45.
Goggins M (2005). J Clin Oncol, 23, 4524-31.
Golden A et al., (1986). Proc Natl Acad Sci USA, 83, 852-6.

Gorg A et al. (2004). Proteomics, 4, 3665-85.
Graham D R et al. (2005). J Physiol, 563, 1-9.
Gronborg M et al. (2006). Mol Cell Proteomics, 5, 157-71.
Harris R et al. (2004). Drug Development Research. 61, 137-154.
He P et al., (2007). Cancer Sci. 98: 1234-1240.
Hellman U et al. (1995). Anal Biochem, 224, 451-5.
Honda K et al. (2005). Cancer Res, 65, 10613-22.
Hong S H et al. (2004). Cancer Res, 64, 5504-10.
Ishii T and Uchida K (2004). Chem Res Toxicol, 17, 1313-22.
Iwabata H et al. (2005). Proteomics, 5, 4653-64.
Jain M et al., (2007). Trends Biotechnol. 25: 307-16.
Jimeno A and Hidalgo M (2006). Mol Cancer Ther, 5, 787-96.
Johnson R et al., (2005). Methods. 35: 223-36.
Kalume D E et al. (2003). Curr Opin Chem Biol, 7, 64-9.
Kanamoto T et al. (2002). Embo J, 21, 1219-30.
Kanski J et al. (2005). Am J Physiol Heart Circ Physiol, 288, H371-81.
Kapphahn R et al. (2006). Exp Eye Res. 83: 165-75.
Kemp E H et al. (2002). Biochem Biophys Res Commun, 298, 169-77.
Kim S et al., (2005). Mol Cells. 20: 17-29.
Kinloch A et al. (2005). Arthritis Res Ther, 7, R1421-9.
Klade C S et al. (2001). Proteomics, 1, 890-8.
Kleef J et al., (2006). Pancreas. 33: 111-118.
Koomen J M et al. (2005). Clin Cancer Res, 11, 1110-8.
Koopmann J et al. (2004). Clin Cancer Res, 10, 2386-92.
Kumar Y et al. (2004). Proteomics, 4, 1672-83.
Laffly E and Sodoyer R, (2005). Hum Antibodies. 14: 33-55.
Laheru D and Jaffee E, (2005). Nat Rev Cancer. 5: 459-67.
Lee L et al. (2002). Anticancer Res. 22: 1615-27.
Lee T et al. (2006). Nucleic Acids Res. 34: D622-7.
Leung T et al. (2005). World J. Gastroenterol. 11: 5075-8.
Levitzki A and Mishani E. (2006). Annu Rev Biochem. 75: 93-109.
Lichtenfels R et al. (2003). Biochim Biophys Acta. 1646: 21-31.
Lobo E et al., (2004). J Pharm Sci. 93: 2645-68.
Logtenberg T, (2007). Trends Biotechnol. Doi :10.1016/j.tibtech.2007.07.005.
Lopez-Alemany R et al. (2003). Thromb Haemost. 90: 724-33.
Lubcc G et al. (2003). Prog Neurobiol. 69: 193-211.
Machida K et al. (2003). Mol Cell Proteomics. 2: 215-33.
Mandell J W. (2003). Am J. Pathol. 163: 1687-98.
Mann M et al. (2002). Trends Biotechnol. 20: 261-8.
Marcus K et al. (2000). Electrophoresis. 21: 2622-36.
Mikuriya K et al., (2007). Int J Oncol. 30: 849-855.
Molina H et al., (2007). Proc. Natl. Acad. Sci. U.S.A. 104: 2199-2204.
Moscato S et al. (2000). Eur J. Immunol. 30 : 3575-84.
Mouneimne G et al. (2004). J. Cell Biol. 166: 697-708.
Nakanishi T et al., (2006). J Chromatogr B Analyt Tec Biomed Life Sci. 838: 15-20.
Nilsson J et al., (1997). Protein Expr Purif. 11: 1-16.
O'Dwyer D et al. (2002). Arch Physiol Biochem. 110: 94-8.
Okusaka T et al., (2006). JOP J. Pancreas. 7: 332-6.
Pancholi V. (2001). Cell Mol Life Sci. 58 : 902-20.
Perluigi M et al. (2005). Mol Cell Proteomics. 4 : 1849-61.
Piast M et al. (2005). Acta Biochim Pol. 52 : 507-13.
Qin Y et al. (995). Int J. Cancer. 60: 694-700.
Rodriguez J A et al. (2005). World J. Surg. 29: 297-305.
Rosty C and Goggins M (2005). Methods Mol. Med. 103: 189-97.
Rubio-Viqueira B et al., (2006). Clin Cancer Res. 12: 4652-61.
Rush J et al. (2005). Nat Biotechnol, 23, 94-101.
Sato N et al. (2000). Cancer Chemother Pharmacol. 46 Suppl: S86-90.
Schmelzle K and White F (2006). Curr Opin Biotechnol, 17: 406-14.
Schoumacher R et al. (1990). Proc Natl Acad Sci USA. 87: 4012-6.
Shen J et al. (2004). Cancer Res, 64, 9018-26.
Shevehenko A et al. (1996). Anal Chem. 68 : 850-8.
Shin S et al. (2004). Proteomics. 4: 3359-68.
Sinha P et al. (1999). Electrophoresis. 20: 2952-60.
Soule H et al., (1973). J Natl Cancer Inst. 51: 1409-16.
Stasyk T et al. (2005). Mol Biol Cell. 16: 4765-80.
Szepeshazi K et al. (2005). Pancreas. 31: 275-82.
Takata T et al. (2006). Biochem Biophys Res Commun, 344: 263-71.
Tanaka Y et al. (2006). Microbiol Immunol. 50: 117-26.
Terrier B et al., (2007). Autoimm Reviews. 6: 176-182.
Unwin R D et al. (2003). Proteomics. 3: 45-55.
Walter M et al. (1995). J Autoimmun. 8: 931-45.
Wu J et al. (2005). Electrophoresis, 26, 225-37.
Xia Q et al. (2005). Biochem Biophys Res Commun. 330: 526-32.
Xue Y et al. (2006). BMC Bioinformatics, 7: 163.
Xue Y et al. (2005). Nucleic Acids Res. 33: W184-7.
Yamagata A et al. (2002). Proteomics. 2: 1267-76.
Yamaguchi H et al. (2005). J. Cell Biol. 168: 441-52.
Yezhelyev M V et al. (2004). Clin Cancer Res. 10: 8028-36.
Yokoi N et al., (2005). Cancer Res. 65: 10371-10380.
Yu Y et al. (2005). Oncology 68: 79-86.
Yunis A et al. (1977). Int J Cancer, 19:128-35.

The invention claimed is:

1. A purified isoform of human alpha-enolase characterized in that it is phosporylated in at least 3 positions, wherein the 3 positions are chosen amongst Threonine 55, Tyrosine 57, Tyrosine 200, Tyrosine 236, Threonine 237, Tyrosine 257, and Serine 419, wherein the at least 3 positions are phosphorylated simultaneously at three different locations of the human alpha-enolase.

2. Methods for the diagnosis of Pancreatic Ductal Adenocarcinoma (PDA), comprising the detection of an isoform of anti-alpha-enolase of claim 1, and/or the detection of an antibody that bind an isoform of anti-alpha-enolase of claim 1.

3. A kit comprising the isoform of alpha-enolase of claim 1, and/or an antibody that bind the isoform of alpha-enolase of claim 1.

* * * * *